(12) United States Patent
Cazelles et al.

(10) Patent No.: US 7,947,701 B2
(45) Date of Patent: May 24, 2011

(54) DUAL MOLECULES CONTAINING PEROXY DERIVATIVE, THE SYNTHESIS AND THERAPEUTIC APPLICATIONS THEREOF

(75) Inventors: Jérôme Cazelles, Balma (FR); Frédéric Cosledan, Labège (FR); Bernard Meunier, Castanet (FR); Alain Pellet, Beaumont sur Lèze (FR)

(73) Assignee: Sanofi-Aventis, Paris (FR)

( * ) Notice: Subject to any disclaimer, the term of this patent is extended or adjusted under 35 U.S.C. 154(b) by 1013 days.

(21) Appl. No.: 11/433,890

(22) Filed: May 12, 2006

(65) Prior Publication Data

US 2007/0021423 A1 Jan. 25, 2007

Related U.S. Application Data

(63) Continuation of application No. PCT/FR2004/002874, filed on Nov. 9, 2004.

(30) Foreign Application Priority Data

Nov. 14, 2003 (FR) ...................................... 03 13371

(51) Int. Cl.
*A61K 31/438* (2006.01)
*C07D 491/113* (2006.01)
(52) U.S. Cl. ........... 514/278; 546/19; 544/363; 514/254
(58) Field of Classification Search .................. 514/278, 514/254; 546/19; 544/363
See application file for complete search history.

(56) References Cited

U.S. PATENT DOCUMENTS 6,949,569 B2 * 9/2005 Meunier et al. ............... 514/313
2004/0038957 A1 2/2004 Meunier et al.

FOREIGN PATENT DOCUMENTS

WO WO 03/000676 1/2003

* cited by examiner

*Primary Examiner* — Charanjit S Aulakh
(74) *Attorney, Agent, or Firm* — Serena Farquharson-Torres

(57) ABSTRACT

The invention relates to dual molecule compounds containing a peroxide derivative, to processes for the synthesis of such compounds, to pharmaceutical compositions comprising such compounds, and to methods of treatment and prevention of malaria comprising administering such compounds and such pharmaceutical compositions.

15 Claims, No Drawings

DUAL MOLECULES CONTAINING PEROXY DERIVATIVE, THE SYNTHESIS AND THERAPEUTIC APPLICATIONS THEREOF

This application is a continuation application of International Application PCT/FR2004/002874, filed Nov. 9, 2004.

The invention relates to dual molecules containing a peroxide derivative, having in particular antimalarial activity, to the synthesis thereof and to the therapeutic applications thereof.

Malaria is one of the primary infectious causes of mortality in the world and affects 100 to 200 million people a year. The significant upsurge in the disease observed in recent years is due to several factors, including:

the carriers, i.e. *Anopheles*, which are becoming resistant to conventional inexpensive insecticides such as DDT (abbreviation for trichloro-1,1,1-bis(p-chlorophenyl)-2, 2-ethane);

the population growth in zones at risk and, mainly, the resistance of many strains of *Plasmodium falciparum*, the parasite responsible for the deadly forms of the disease, to the medicinal products conventionally used, such as chloroquine and mefloquine. The discovery of artemisinin, a powerful antimalarial extracted from *Artemisia annua*, has drawn attention to molecules having, like artemisinin, an endoperoxide function.

Artemisinin and some of its hemisynthetic derivatives, such as artemether and artesunate, have proved to be very active on resistant *P. falciparum* strains. However, the high cost of these natural compounds and uncertain supply represent major disadvantages. Therefore, the advantage of synthetic antimalarial compounds, which would be accessible at low prices and would offer a mechanism of action similar to that of artemisinin, namely an alkylating effect on heme (one of the constituent groups of haemoglobin) and/or parasitic proteins, will be evaluated.

Synthetic peroxides with an antimalarial effect have, for example, been described in PCT International Application WO 03/000676.

The search for compounds having improved pharmacological properties, making them appropriate for use as antimalarial medicinal products, has led the inventors to develop a novel synthesis strategy based on the use of compounds capable both of being effectively accumulated in the parasite and of exerting an effect like that of artemisinin.

The inventors have observed that forming a covalent adduct between a compound having antimalarial properties and a peroxide-type derivative provides coupling products with, surprisingly, a synergistic effect between the penetration capacity and the activity of the respective constituents on chloroquine-resistant strains and, in general, a high efficacy for a wide range of parasites. Such dual molecules, provided in the form of coupling products, are the subject of patent application WO 01/77105.

The inventors have, presently, developed a family of molecules of the type indicated above, but having a small number of stereoisomers, which is an advantage for their use as medicinal products. The invention therefore relates to such dual molecules, to the synthesis thereof and to the biological applications thereof, which prove to be most advantageous for treating parasitic diseases such as malaria.

The dual molecules according to the present invention correspond to formula (I):

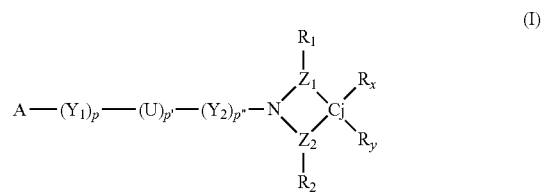

in which:

A represents a residue of a molecule with antimalarial activity and/or a residue that facilitates the bioavailability, p, p' and p" represent, independently of one another, 0 or 1, at least one of p or of p" being equal to 1, $Y_1$ and $Y_2$, which may be identical or different, represent a linear, branched or cyclic $C_1$ to $C_6$ alkylene chain optionally comprising one or more amine, amide, thioamide, sulphonyl, sulphonate, sulphonamide, carbonyl, thiocarbonyl, carboxyl, thiocarboxyl, ether or thioether radicals, this alkylene chain being optionally substituted with one or more groups chosen from halogen atoms, hydroxyl groups, acetal groups and linear, branched or cyclic $C_1$ to $C_5$ alkyl radicals, U represents an amine, amide, thioamide, sulphonyl, sulphonate, sulphonamide, carbonyl, thiocarbonyl, carboxyl, thiocarboxyl, ether or thioether radical, $Z_1$ and $Z_2$, which may be identical or different, represent a saturated or unsaturated, linear, branched or cyclic $C_1$ to $C_4$ alkylene radical, one of $Z_1$ or $Z_2$ possibly being absent, or $Z_1+Z_2$ together represent a polycyclic structure including N and the junction carbon Cj, $R_1$ and $R_2$, which may be identical or different, represent a hydrogen atom or a functional group capable of increasing the water-solubility of the dual molecule, $R_x$ and $R_y$ together form a cyclic peroxide containing from 4 to 8 ring members and comprising 1 or 2 additional oxygen atoms in the cyclic structure (i.e. a total of 3 to 4 oxygen atoms in the ring), Cj being one of the ring members of this cyclic peroxide, said cyclic peroxide being substituted with 1 to 8 groups $R_3$, which may be identical or different from one another, occupying any positions on the carbon atoms of the peroxide ring and being chosen from the following atoms and groups:

hydrogen, halogen, —OH, —$CF_3$, —$NO_2$, aryl (for example phenyl) or heteroaryl (for example pyridinyl), alkyl or —O-alkyl (said alkyl groups containing from 1 to 10 carbon atoms and being linear, branched or cyclic), or a $C_3$ to $C_{18}$ mono-, bi- or tricyclic structure which may also contain one or more (for example from 1 to 6) hetero atoms chosen from oxygen, nitrogen and sulphur, optionally substituted with one or more groups chosen from halogen atoms, hydroxyl groups and linear, branched or cyclic $C_1$ to $C_6$ alkyl groups; examples of such cyclic structures are cycloalkyl groups (such as cyclopropyl, cyclobutyl, cyclopentyl, cyclohexyl, cycloheptyl and cyclooctyl groups) and the adamantyl group (tricyclic structure containing 10 carbon atoms), at least one of the groups $R_3$ being different from a hydrogen atom, it being possible for two groups $R_3$ carried by adjacent carbon atoms on the peroxide ring to form together a saturated or unsaturated 5- or 6-membered cyclic structure optionally substituted in any positions with one or more (for example from 1 to 3) substituents $R_3$ as described above, it being possible for two groups $R_3$ carried by the same carbon atom of the peroxide ring to form together a mono-, bi- or tricyclic structure as defined above (which will therefore be located in the spiro-position on the peroxide ring).

Advantageously, the residue A brings into the parasite the compound of formula (I) according to the invention, which then exerts an alkylating effect on the heme and/or the parasitic proteins.

The compounds of formula (I) can exist in the form of bases or of addition salts with acids. Such addition salts are also part of the invention. These salts are advantageously prepared with pharmaceutically acceptable acids, but the salts of other acids that are useful, for example, for purifying or isolating the compounds of formula (I) are also part of the invention.

The compounds according to the invention can also exist in the form of hydrates or of solvates, i.e. in the form of associations or of combinations with one or more molecules of water or with a solvent. Such hydrates and solvates are also part of the invention.

The invention is also directed towards the racemic mixtures and the optically pure isomers of the molecules of formula (I), and also mixtures in any proportions of said optically pure isomers. It is also directed towards the achiral molecules.

In the definition of the compounds of formula (I) above, and in the subsequent text, unless otherwise indicated in the text:

the term "halogen atom" is intended to mean: an F, Cl, Br or I atom, the term "alkyl group" is intended to mean: a monovalent group originating from the removal of a hydrogen atom from the molecule of a hydrocarbon (such as an ethyl group of formula —$C_2H_5$), the term "alkylene radical or chain" is intended to mean: a divalent group originating from the removal of two hydrogen atoms from two different carbon atoms of a hydrocarbon (such as, for example, an ethylene chain of formula —$CH_2$—$CH_2$—), the term "acetal group" is intended to mean: a cyclic or non-cyclic acetyl group. By way of examples, mention may be made of dimethoxyl, diethoxyl, ethane-1,2-dioxyl, propane-1,3-dioxyl and 2,2-dimethylpropane-1,3-dioxyl groups, corresponding respectively to the following formulae:

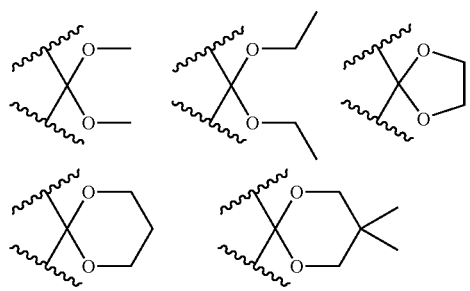

the expression "residue that facilitates the bioavailability" is intended to mean: a saturated or unsaturated $C_6$-$C_{18}$ cyclic molecule, or an optionally substituted linear $C_1$-$C_{18}$ chain, said molecule and said chain comprising one or more hetero atoms chosen from N, O and S. By way of examples of residues that facilitate the bioavailability, mention may be made of guanidinium, morpholino, peptide or polyamine residues, the expression "functional group capable of increasing the water-solubility of the dual molecule" is intended to mean: a group advantageously chosen from —COOH, —OH and —$N(R_a,R_b)$ with $R_a$ and $R_b$, which may be identical or different, representing a hydrogen atom or a linear, branched or cyclic $C_1$ to $C_5$ alkyl radical, the term "amine radical" is intended to mean: a group of formula —$NR_a$—, where $R_a$ is as defined above, the term "amide radical" is intended to mean: a group of formula —$NR_a$—CO— or —CO—$NR_a$—, where $R_a$ is as defined above, the term "thioamide radical" is intended to mean: a group of formula —$NR_a$—CS— or —CS—$NR_a$—, where $R_a$ is as defined above, the term "sulphonyl and sulphonate radicals" is intended to mean: groups of respective formulae —$SO_2$— and —$SO_3$—, the term "sulphonamide radical" is intended to mean: a group of formula —$NR_a$—$SO_2$— or —$SO_2$—$NR_a$—, where $R_a$ is as defined above, the term "carboxyl radical" is intended to mean: a group of formula —CO—O— or —O—CO—, the term "thiocarboxyl radical" is intended to mean: a group of formula —CS—O— or —O—CS—, the term "carbonyl and thiocarbonyl radicals" is intended to mean: groups of respective formulae —CO— and —CS—, the term "ether and thioether radicals" is intended to mean: groups of respective formulae —O— and —S—.

In the compounds of formula (I) according to the invention, A can represent a nitrogenous heterocycle of formula (II):

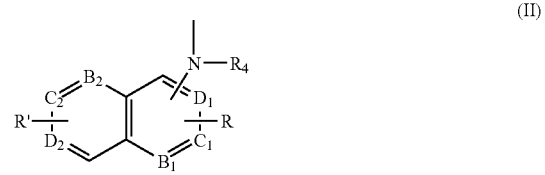

in which:

R and R', which may be identical or different, each represent one or more (for example 1 to 3) substituents occupying distinct positions on the rings to which they are attached, chosen from hydrogen or halogen atoms and the groups —OH, —$CF_3$, aryl (such as phenyl), heteroaryl (such as pyridinyl), alkyl or —O-alkyl (said alkyl groups containing from 1 to 5 carbon atoms and being linear, branched or cyclic), —$NO_2$ or —$N(R_a,R_b)$, where $R_a$ and $R_b$, which may be identical or different, represent hydrogen atoms or alkyl groups containing from 1 to 5 carbon atoms and being linear, branched or cyclic; at least one of R or R' being different from a hydrogen atom;

$R_4$ represents a hydrogen atom or a linear, branched or cyclic $C_1$ to $C_5$ alkyl radical, or $R_4$ forms, with a carbon or nitrogen atom present in the group —$(Y_1)_p$—$(U)_{p'}$—$(Y_2)_{p''}$— of formula (I), a ring comprising from 5 to 8 ring members (for example a piperazinyl ring), the radicals $B_1$, $C_1$, $D_1$, $B_2$, $C_2$ and $D_2$ represent nitrogen atoms or —CH═ ring members, given that either one of the radicals $B_1$, $C_1$ and $D_1$ represents a nitrogen atom and the other radicals represent —CH═ ring members, or one of the radicals $B_2$, $C_2$ and $D_2$ represents a nitrogen atom and the other radicals represent —CH═ ring members, or one of the radicals $B_1$, $C_1$ and $D_1$ and one of the radicals $B_2$, $C_2$ and $D_2$ represent nitrogen atoms and the other radicals represent —CH= ring members.

The nitrogenous heterocycle of formula (II) can in particular be chosen from an aminoquinoline of formula (IIa) or a 1,5-naphthyridine of formula (III), below:

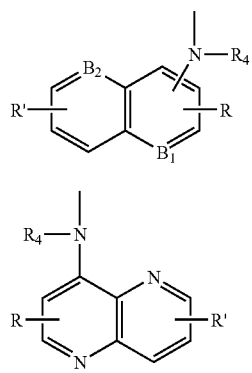

(IIa)

(III)

in which R, $R_1$ and $R_4$ are as defined above and either $B_1$ represents a nitrogen atom and $B_2$ represents a —CH= ring member or $B_1$ represents a —CH= ring member and $B_2$ represents a nitrogen atom.

Among the aminoquinolines of formula (IIa), mention may also be made of the aminoquinolines of formulae (IIb) and (IIc), in which R, $R_1$ and $R_4$ are as defined above:

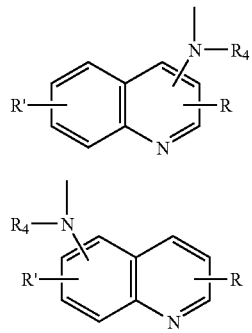

(IIb)

(IIc)

In the compounds of formula (I) according to the invention, A can also represent a group of formula (IV):

$R_5$—CHOH—                                              (IV)

in which $R_5$ represents an aryl radical (for example a 9-phenanthrenyl) or a nitrogenous heterocyclic residue (for example a 4-quinolinyl) optionally substituted with one or more (for example from 1 to 3) groups R as defined above.

In the compounds of formula (I) according to the invention, A can also represent a 2-(aminomethyl)phenol residue of formula (V), a biguanide residue chosen from the proguanil derivatives of formula (VI), a cycloguanil derivative of formula (VII), a pyrimidine residue, and more particularly a pyrimethamine residue of formula (VIII) or (IX), or an acridine residue of formula (X), in which formulae R, R', $R_a$ and $R_b$ are as defined above:

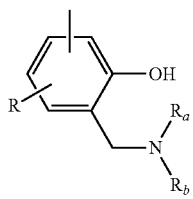

(V)

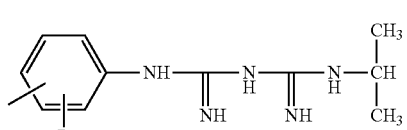

(VI)

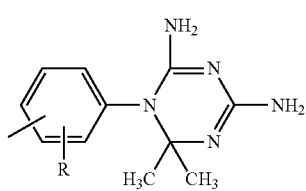

(VII)

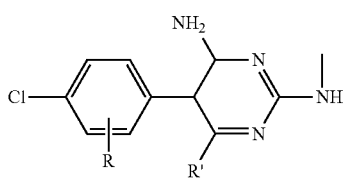

(VIII)

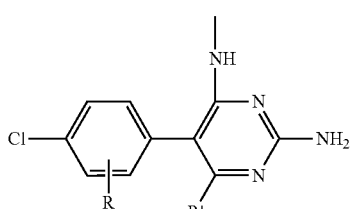

(IX)

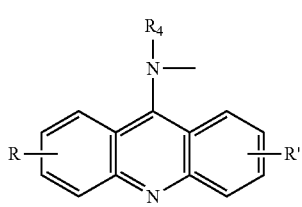

(X)

Thus, according to the nature of the residue A, various subgroups of compounds of formula (I) can be obtained.

For example, when A represents a nitrogenous heterocycle of formula (II) as defined above, then compounds according to the invention corresponding to formula (Ia) are obtained:

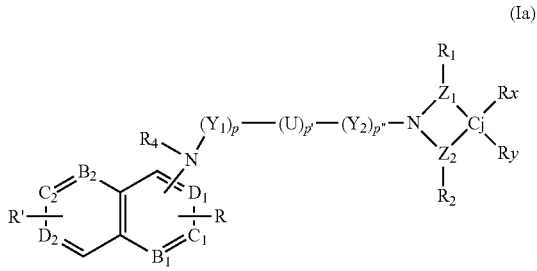

(Ia)

In particular, when A represents a nitrogenous heterocycle of aminoquinoline type, according to formula (IIa) as defined above, then compounds according to the invention corresponding to formula (Ib) are obtained:

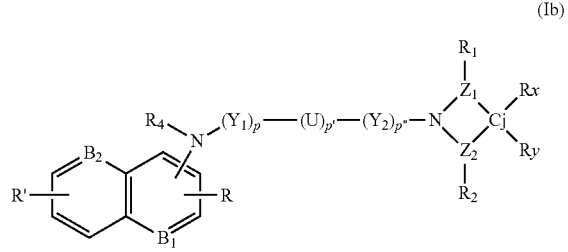

(Ib)

Among the dual molecules of formula (I) in accordance with the invention, mention may more especially be made of those in which $R_x$ and $R_y$ together form a cyclic peroxide containing 5 or 6 ring members and comprising 1 additional oxygen atom in the cyclic structure (i.e. a total of 3 oxygen atoms in the ring), Cj being one of the ring members of this cyclic peroxide, said cyclic peroxide being substituted with 1 to 4 groups $R_3$, which may be identical or different, as defined above.

Such peroxide rings may in particular consist of:

trioxanes of formula (XI):

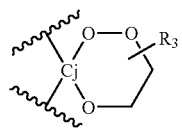

(XI)

in which $R_3$ represents 1 to 4 groups, which may be identical or different, as defined above, or trioxolanes of formula (XII):

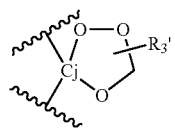

(XII)

in which $R_{3'}$ represents 1 or 2 groups, which may be identical or different, chosen from the following atoms and groups:

hydrogen, halogen, —OH, —CF$_3$, —NO$_2$, aryl (for example phenyl) or heteroaryl (for example pyridinyl), alkyl or —O-alkyl (said alkyl groups containing from 1 to 10 carbon atoms and being linear, branched or cyclic), or a $C_3$ to $C_{18}$ mono-, bi- or tricyclic structure which may also contain 1 or more (for example from 1 to 6) hetero atoms chosen from oxygen, nitrogen and sulphur, optionally substituted with one or more groups chosen from halogen atoms, hydroxyl groups and linear, branched or cyclic $C_1$ to $C_6$ alkyl groups; examples of such cyclic structures are cycloalkyl groups (such as cyclopropyl, cyclobutyl, cyclopentyl, cyclohexyl, cycloheptyl and cyclooctyl groups) and the adamantyl group (tricyclic structure containing 10 carbon atoms);

at least one of the groups $R_3$, being different from a hydrogen atom, it being possible for two groups $R_3$, carried by the same carbon atom of the peroxide ring to form together a mono-, bi- or tricyclic structure as defined above (which will therefore be located in the spiro-position on the peroxide ring).

In formulae (XI) and (XII), the carbon Cj is as defined in formula (I), i.e. it corresponds to the junction carbon between the cyclic peroxide and the heterocycle formed between the nitrogen atom, the carbon Cj and the radicals $Z_1$ and $Z_2$ Among the trioxanes of formula (XI), mention may in particular be made of those corresponding to formula (XIa):

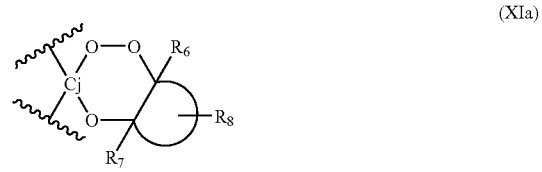

(XIa)

in which the arc of the circle represents a saturated or unsaturated 5- or 6-membered cyclic structure, Cj is as defined above, and $R_6$, $R_7$ and $R_8$, which may be identical or different from one another, are chosen from the following atoms and groups: hydrogen, halogen, —OH, —CF$_3$, —NO$_2$, aryl (for example phenyl) or heteroaryl (for example pyridinyl), alkyl or —O-alkyl (said alkyl groups containing from 1 to 10 carbon atoms and being linear, branched or cyclic).

In formula (XIa), $R_6$, $R_7$ and $R_8$ advantageously represent hydrogen atoms or linear or branched $C_1$-$C_{10}$ alkyl groups.

Among the trioxanes of formula (XI), mention may also be made of those corresponding to formula (XIb), in which Cj is as defined above and $R_6$, $R_7$ and $R_8$ are as defined in relation to formula (XIa):

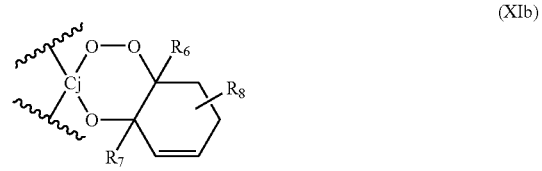

(XIb)

Among the trioxanes of formula (XI), mention may also be made of those corresponding to formula (XIc):

(XIc)

in which Cj is as defined above and $R_{3'}$ represents 1 to 4 groups, which may be identical or different from one another, occupying any positions on the carbon atoms of the peroxide ring and being chosen from the following atoms and groups:

hydrogen, halogen, —OH, —CF$_3$, —NO$_2$, aryl (for example phenyl) or heteroaryl (for example pyridinyl), alkyl or —O-alkyl (said alkyl groups containing from 1 to 10 carbon atoms and being linear, branched or cyclic), or a $C_3$ to $C_{18}$ mono-, bi- or tricyclic structure which may also contain 1 or more (for example from 1 to 6) hetero atoms chosen from oxygen, nitrogen and sulphur, optionally substituted with one or more groups chosen from halogen atoms, hydroxyl groups and linear, branched or cyclic $C_1$ to $C_6$ alkyl groups; examples of such cyclic structures are cycloalkyl groups (such as cyclopropyl, cyclobutyl, cyclopentyl, cyclohexyl, cycloheptyl and cyclooctyl groups) and the adamantyl group (tricyclic structure containing 10 carbon atoms);

at least one of the groups $R_{3'}$ being different from a hydrogen atom, it being possible for two groups $R_{3'}$ carried by the same carbon atom of the peroxide ring to form together a mono-, bi- or tricyclic structure as defined above (which will therefore be located in the spiro-position on the peroxide ring).

In formula (XIc), $R_{3''}$ advantageously represents 1 to 4 groups chosen from hydrogen atoms and linear or branched $C_1$-$C_{10}$ alkyl groups, or two groups $R_{3''}$ carried by the same carbon atom of the peroxide ring form together a mono-, bi- or tricyclic structure as defined above.

The invention is in particular directed towards the dual molecules corresponding to the coupling product comprising an aminoquinoline of formula (IIa) and a peroxide structure of formula (XI); such molecules correspond to formula (XIII), in which R, R', $B_1$, $B_2$, $Y_1$, U, $Y_2$, p, p', p'', $Z_1$, $Z_2$, Cj, $R_1$, $R_2$, $R_3$ and $R_4$ are as defined above:

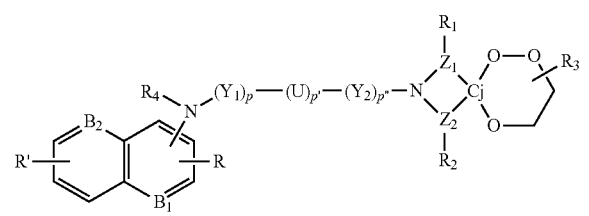

(XIII)

The invention is also directed towards the dual molecules corresponding to the coupling product comprising an aminoquinoline of formula (IIa) and a peroxide structure of formula (XIa); such molecules correspond to formula (XIIIa), in which R, R', $B_1$, $B_2$, $Y_1$, U, $Y_2$, p, p', p'', $Z_1$, $Z_2$, $C_j$, $R_1$, $R_2$, $R_4$, $R_6$, $R_7$ and $R_8$ are as defined above:

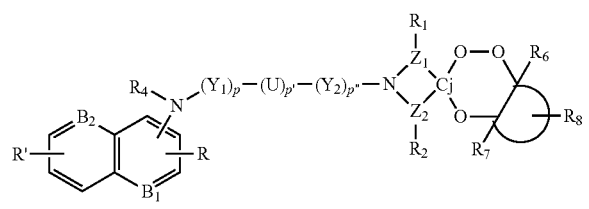

(XIIIa)

The invention is also directed towards the dual molecules corresponding to the coupling product comprising an aminoquinoline of formula (IIa) and a peroxide structure of formula (XIb); such molecules correspond to formula (XIIIb), in which R, R', $B_1$, $B_2$, $Y_1$, U, $Y_2$, p, p', p'', $Z_1$, $Z_2$, Cj $R_1$, $R_2$, $R_4$, $R_6$, $R_7$ and $R_8$ are as defined above:

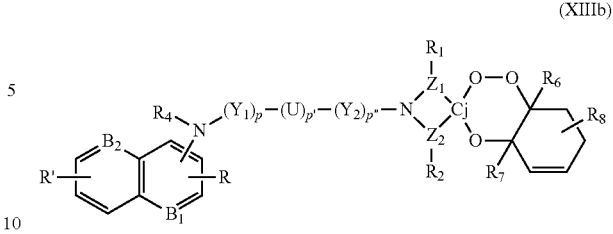

(XIIIb)

The invention is also directed towards the dual molecules corresponding to the coupling product comprising an aminoquinoline of formula (IIa) and a peroxide structure of formula (XIc); such molecules correspond to formula (XIIIc), in which R, R', $B_1$, $B_2$, $Y_1$, U, $Y_2$, p, p', p'', $Z_1$, $Z_2$, $C_j$, $R_1$, $R_2$, $R_{3''}$ and $R_4$ are as defined above:

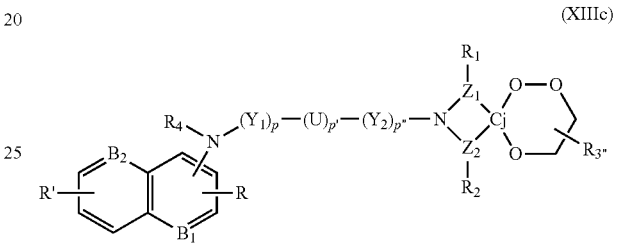

(XIIIc)

The invention is also directed towards the dual molecules corresponding to the coupling product comprising an aminoquinoline of formula (IIa) and a peroxide structure of formula (XII); such molecules correspond to formula (XIV), in which R, R', $B_1$, $B_2$, $Y_1$, U, $Y_2$, p, p', p'', $Z_1$, $Z_2$, $C_j$, $R_1$, $R_2$, $R_3$, and $R_4$ are as defined above:

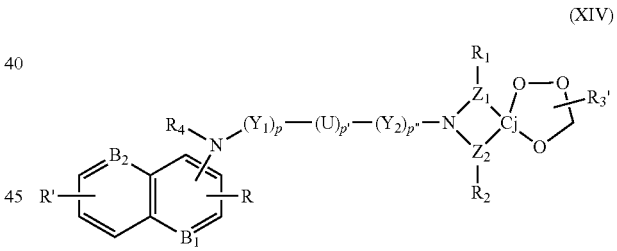

(XIV)

In the various formulae defined above, R and R' are advantageously such that:

R and R' represent a single substituent, i.e. either R or R' represents a hydrogen atom and the other of R and R' is chosen from halogen atoms and the groups —$CF_3$, —$N(R_a,R_b)$ and —O-alkyl, where the alkyl group is a linear, branched or cyclic $C_1$ to $C_5$ alkyl group, $R_a$ and $R_b$ being as defined above, or R and R' each represent a group chosen from halogen atoms and the groups —$CF_3$, —$N(R_a,R_b)$ and —O-alkyl, where the alkyl group is a linear, branched or cyclic $C_1$ to $C_5$ alkyl group, $R_a$ and $R_b$ being as defined above.

As regards the group of formula —$(Y_1)_p$—$(U)_{p'}$—$(Y_2)_{p''}$, present in the molecules of formula (I) as a coupling arm between the residue A and the cyclic peroxide formed by $R_x$ and $R_y$, it is advantageously chosen so as to modulate the water-solubility of the molecule, in order to confer on it optimal activity.

In this regard, mention may in particular be made of the molecules of formula (I) according to the invention in which p, p' and p" are as defined above and:
- $Y_1$ and $Y_2$, which may be identical or different, represent a linear, branched or cyclic $C_1$ to $C_6$ alkylene chain optionally comprising one or more amine, amide, carbonyl or ether radicals, this alkylene chain being optionally substituted with one or more groups chosen from halogen atoms, hydroxyl groups, acetal groups and linear, branched or cyclic $C_1$ to $C_5$ alkyl radicals,
- U represents an amine, amide, carbonyl, carboxyl or ether radical.

Mention may also be made of the molecules of formula (I) according to the invention in which:
- either p'=p"=0, p=1 and $Y_1$ represents a linear, branched or cyclic (advantageously linear or branched) $C_1$ to $C_6$ alkylene chain optionally substituted as described above,
- or p=p'=1, p"=0, $Y_1$ represents a linear, branched or cyclic (advantageously linear or branched) $C_1$ to $C_6$ alkylene chain optionally substituted as described above, and U represents an amine, amide, carbonyl, carboxyl or ether radical,
- or p=p'=p"=1, $Y_1$ and $Y_2$ represent linear, branched or cyclic (advantageously linear or branched) $C_1$ to $C_6$ alkylene chains optionally substituted as described above, and U represents an amine, amide, carbonyl, carboxyl or ether radical.

Other molecules of formula (I) according to the invention are such that $Z_1$ and $Z_2$, which may be identical or different, each represent a linear or branched $C_1$ to $C_4$ alkylene radical. Mention may in particular be made of the molecules of formula (I) according to the invention in which $Z_1$ and $Z_2$ each represent an ethylene radical, so as to form a piperidinyl ring with the nitrogen atom and the junction carbon Cj.

The various definitions given below for each of the constituent groups of formula (I) can be taken in combination with one another, so as to form various subgroups of dual molecules according to the invention. Mention may in particular be made of the dual molecules corresponding to formula (XV) or (XVI), in which R, R', $B_1$, $B_2$, $Y_1$, U, $Y_2$, p, p', p", $R_1$, $R_2$, $R_3$, $R_3'$, and $R_4$ are as defined above:

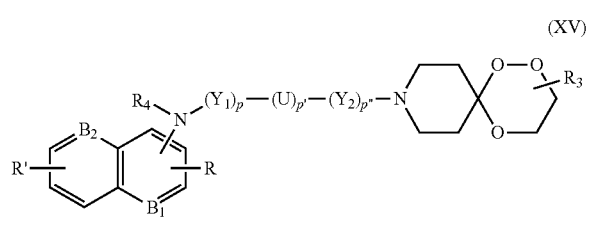

(XV)

(XVI)

Another subgroup of compounds of formula (I) in accordance with the invention may be such that:
- A represents a residue of a molecule with antimalarial activity and/or a residue that facilitates the bioavailability, the latter having one or more hetero atoms chosen from N, O and S in a saturated or unsaturated $C_6$-$C_{18}$ cyclic molecule or in a substituted or unsubstituted linear $C_1$-$C_{18}$ chain, such as a guanidinium, morpholino, peptide or polyamine residue,
- p, p' and p" represent, independently of one another, 0 or 1, at least one of p or of p" being equal to 1,
- $Y_1$ and $Y_2$, which may be identical or different, represent a linear or branched $C_1$ to $C_5$ alkylene chain, containing, where appropriate, one or more amine, amide, sulphonamide, carboxyl, thiocarboxyl, carbonyl, ether, thioether or thiocarbonyl radicals, this $C_1$ to $C_5$ alkylene chain being, where appropriate, substituted with a linear or branched $C_1$ to $C_5$ alkyl radical,
- U is an amine, amide, thioamide, sulphonyl, carbonyl, thiocarbonyl, carboxyl, thiocarboxyl (C(O)=S), ether, thioether or sulphonate ($SO_3$) function,
- $Z_1$ and $Z_2$, which may be identical or different, represent a saturated or unsaturated, linear, branched or cyclic $C_1$ to $C_4$ alkylene radical, one of $Z_1$ or $Z_2$ possibly being absent, or $Z_1+Z_2$ together represent a polycyclic structure including N and the junction carbon Cj,
- $R_1$ and $R_2$, which may be identical or different, represent a hydrogen atom or a functional group capable of increasing the water-solubility of the dual molecule, advantageously chosen from —COOH, —OH, —N($R_a$,$R_b$) with $R_a$ and $R_b$, which may be identical or different, representing a hydrogen atom or a linear, branched or cyclic $C_1$ to $C_5$ alkyl radical,
- $R_x$ and $R_y$ together form a cyclic peroxide containing from 4 to 8 ring members and comprising 1 or 2 additional oxygen atoms in the cyclic structure (i.e. a total of 3 or 4 oxygen atoms in the ring), Cj being one of the ring members of this cyclic peroxide, said cyclic peroxide being substituted with 1 to 4 groups $R_3$, which may be identical or different from one another, occupying any positions on the carbon atoms of the peroxide ring and being chosen from the following atoms and groups: hydrogen, halogen, —OH, —$CF_3$, —$NO_2$, aryl or heteroaryl (for example a phenyl or a pyridine), alkyl or —O-alkyl, said alkyl groups containing from 1 to 6 carbon atoms and being linear, branched or cyclic, a $C_3$ to $C_{18}$ mono-, bi- or tricyclic structure which may also contain one or more (for example from 1 to 6) hetero atoms chosen from oxygen, nitrogen and sulphur, optionally substituted with a linear, branched or cyclic $C_1$ to $C_6$ alkyl group; examples of such cyclic structures are the cyclohexyl or adamantyl groups (tricyclic structure containing 10 carbon atoms),
- at least one of the groups $R_3$ being different from a hydrogen atom,
- it being possible for two adjacent groups $R_3$ on the peroxide ring to form together a saturated or unsaturated 5- or 6-membered cyclic structure, optionally substituted in any positions with one or more (for example from 1 to 3) substituents $R_3$ as defined above.

A subject of the invention is also a process for preparing the molecules of formula (I) defined above. This method comprises reacting reactive derivatives of A (such as halogenated derivatives) and peroxide derivatives comprising the residues $R_x$ and $R_y$, so as to form, between these derivatives, a coupling arm —($Y_1$)$_p$—(U)$_{p'}$—($Y_2$)$_{p''}$— as defined in relation to formula (I).

Various synthetic pathways will be readily accessible to those skilled in the art by carrying out the reactions according to conventional techniques. For the synthesis of the peroxide derivatives comprising the residues $R_x$ and $R_y$, reference will be made, for example, to the work by S. Pataï: "The Chemistry of Peroxides", John Wiley and Sons Ltd., 1983.

Thus, to prepare dual molecules of formula (I) containing, as residue A, an aminoquinoline of formula (IIa) as defined above, a compound of formula (XVII):

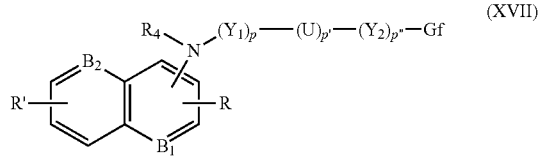
(XVII)

in which R, R', $B_1$, $B_2$, $R_4$, $Y_1$, $Y_2$, U, p, p' and p" are as defined in formulae (I) and (IIa) above and Gf represents a functional group (advantageously, a hydroxyl group or a leaving group, such as a halogen atom), can be reacted with a compound of formula (XVIII), in which $Z_1$, $Z_2$, $R_1$, $R_2$, Cj, $R_x$ and $R_y$ are as defined in formula (I):

(XVIII)

The compounds according to the invention corresponding to formula (Ib), as defined above, are thus obtained.

Alternatively to obtain the compounds of formula (I) in which p=1 and which contain, as residue A, an aminoquinoline of formula (IIa), a compound of formula (XIX):

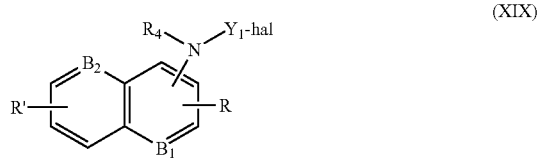
(XIX)

in which R, R', $B_1$, $B_2$, $R_4$ and $Y_1$ are as defined in formulae (I) and (IIa) above, and "hal" represents a halogen atom, can be reacted with a compound of formula (XX), in which U, $Y_2$, p', p", $Z_1$, $Z_2$, $R_1$, $R_2$, $C_j$, $R_x$ and $R_y$ are as defined in formula (I) (advantageously, p'=1 and U=—NH_2):

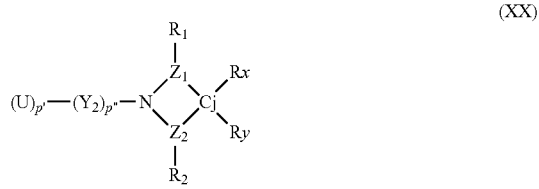
(XX)

To obtain the compounds of formula (I) in which p=p'=1, p"=0 and U represents an amide radical of formula —NH—CO—, an alternative may consist in reacting a compound of formula (XVIII) as defined above with phosgene or a phosgene derivative (such as triphosgene), and then with a compound of formula (XXI), in which R, R', $B_1$, $B_2$, $R_4$ and $Y_1$ are as defined in formulae (I) and (IIa) above:

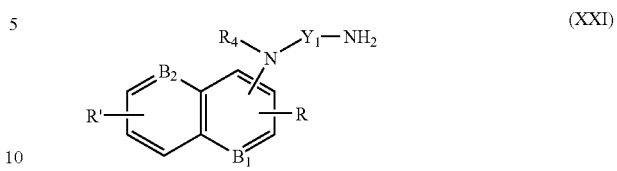
(XXI)

Moreover, to obtain the compounds of formula (I) in which p=p'=1, p"0 and U represents a carboxyl radical of formula —O—CO—, an alternative may consist in reacting a compound of formula (XXII):

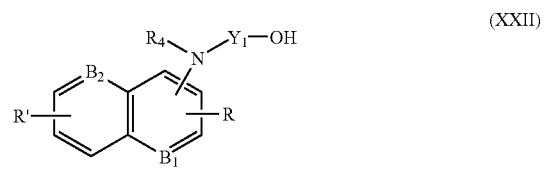
(XXII)

in which R, R', $B_1$, $B_2$, $R_4$ and $Y_1$ are as defined in formulae (I) and (IIa) above with phosgene or a phosgene derivative (such as triphosgene), and then with a compound of formula (XVIII) as defined above.

The coupling reactions described above for obtaining the compounds of formula (I) in accordance with the invention are advantageously carried out in a polar solvent, in the presence of an organic or inorganic base and at ambient temperature.

The coupling reaction is followed, where appropriate, by a reaction with a pharmaceutically acceptable acid, so as to obtain the coupling product in the form of a salt. With this aim, the basic nitrogens are protonated by adding a pharmaceutically acceptable organic or inorganic acid. By way of examples of pharmaceutically acceptable organic salts, mention will be made of citric acid salts, tartaric acid salts, fumaric acid salts and lactic acid salts. By way of examples of pharmaceutically acceptable inorganic salts, mention will be made of hydrochloric acid salts and phosphoric acid salts. The reaction can be carried out with 2 equivalents of acid. The protonated product is then recovered and subjected to one or more purification steps if necessary.

To obtain the intermediates of the formula (XIX) defined above, the following may be carried out:

a) a compound of formula (XXIII):

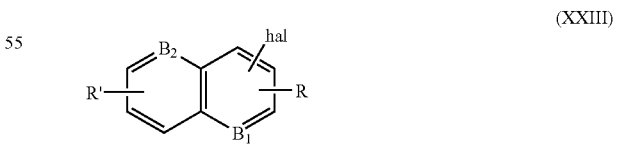
(XXIII)

in which R, R', $B_1$ and $B_2$ are as defined above in formula (IIa) and "hal" represents a halogen atom, is reacted with an amino derivative of formula $R_4$—NH—$Y_1$—$U_1$, in which $R_4$ and $Y_1$ are as defined above and $U_1$ represents a group —OH, —Cl, —Br, —I, —NH_2, —NHR_4, —COR_4 or —COOR_4 (advantageously, $U_1$=—OH), which gives a compound of formula (XXIV):

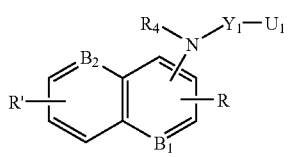

(XXIV)

b) the group $U_1$ is substituted with a halogen ("hal"), advantageously a bromine atom, so as to give the compound of formula (XIX).

Step a) is advantageously carried out at a temperature of 185° C. with stirring. The amino derivative of formula $R_4$—NH—$Y_1$—$U_1$ can be used in a proportion of 5 molar equivalents. After cooling, the product obtained can be precipitated by adding 10% sodium hydroxide and washed with methanol.

Step b) is advantageously carried out by adding an HBr/$H_2SO_4$ mixture at 160° C. for 3 h 30 min. After neutralization, the product is recovered by extraction, for example with toluene.

The compounds of formula (I) according to the invention in which A is as defined above and is different from a group of formula (IIa) can be obtained in a manner similar to the reactions described above, but appropriately replacing the starting compound (XVII), (XIX), (XXI) or (XXII) with another reactive derivative of A, according to the organic chemistry techniques known to those skilled in the art.

A subject of the invention is also compounds of formulae (XVIII) and (XX) defined above. These compounds may be useful as synthesis intermediates of the compounds of formula (I) in accordance with the present invention.

The following examples describe the preparation of certain compounds in accordance with the invention. These examples are not limiting and merely illustrate the present invention. These examples refer to FIGS. 1 to 12, which describe, respectively, the syntheses of the compounds PA 1010, PA 1011, PA 1025 (and its salts PA 1047 and PA 1042), PA 1128, PA 1102, PA 1035, PA 1020, PA 1021 (and its salts PA 1040), PA 1026, PA 1069, PA 1080 and PA 1097.

1—Synthesis of PA 1010, Racemic Mixture

7-Chloro-N-{2-[6-isopropyl-8a-methyl-4a,7,8,8a-tetrahydro-1'H-spiro[1,2,4-benzotrioxine-3,4'-piperidin]-1'-yl]ethyl}quinolin-4-amine

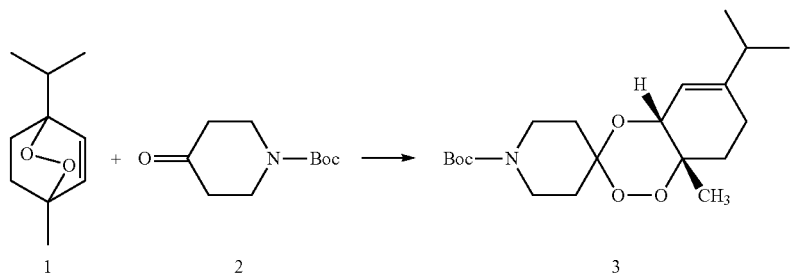

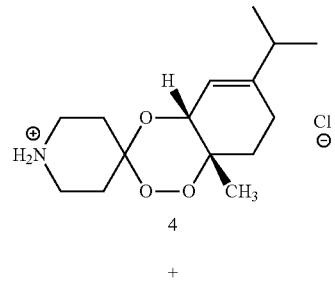

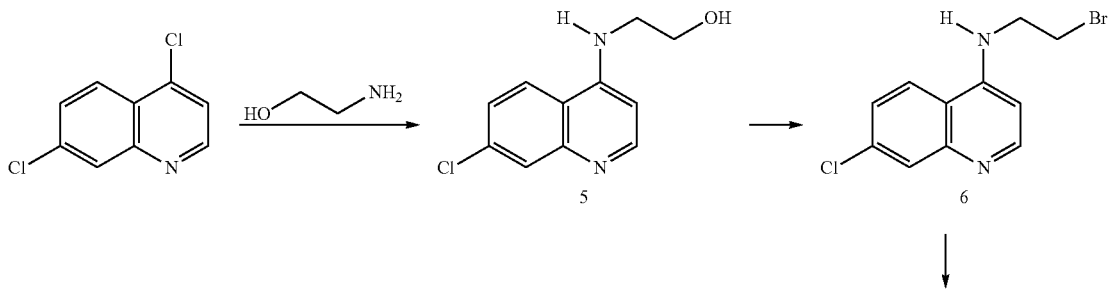

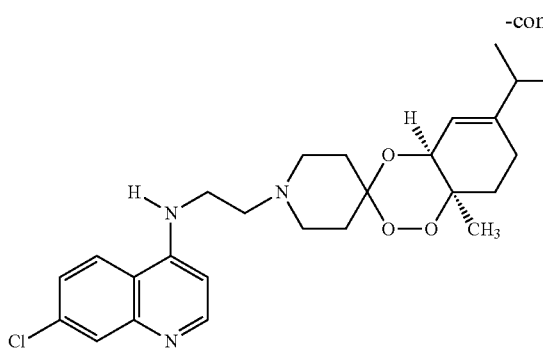
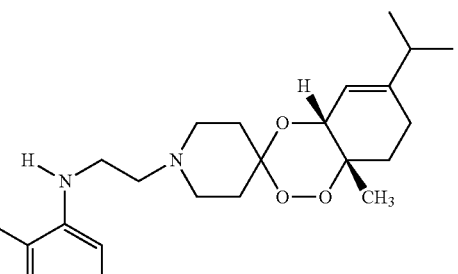

PA 1010

1-1: Synthesis of the Trioxane 3

0.66 g (3.3 mmol) of Boc-piperidone 2 (prepared according to the method described by J. McGuire et al., J. Med. Chem. 1998, 41, 1409-1416) is dissolved in 2 ml of dry dichloromethane, in a round-bottomed flask under an argon atmosphere. The mixture is cooled to −20° C. and 0.46 ml (3.6 mmol) of $BF_3OEt_2$, followed by 0.5 ml (0.33 mmol) of a solution of ascaridole 1, prepared according to the method described by Meunier et al. in PCT International Application WO 01/77105, in the form of a 0.66 M solution in dichloromethane, are added. Every 15 minutes, 42 µl (0.33 mmol) of $BF_3OEt_2$ followed by 0.5 ml (0.33 mmol) of ascaridole 1 are added to this reaction mixture. This fractionated addition operation is repeated a further 8 times. The reaction is then stopped by adding 5 ml of a saturated aqueous $NaHCO_3$ solution and 50 ml of dichloromethane are added. The organic phase is extracted with 100 ml of dichloromethane, dried by adding $Na_2SO_4$ and filtered, and the solvents are evaporated off under vacuum. The residue is then purified by chromatography column ($SiO_2$ 60 $ACC_{6-35}$ µm, eluent: 70/20/10, v/v/v, n-hexane/ether/dichloromethane). The exiting of the products from the column is controlled by TLC ($SiO_2$ 60 F 254, visualized with phosphomolybdic acid) and the trioxane is recovered. The phases containing the trioxane 3 are combined and the solvents are evaporated off, giving an oil identified as the trioxane 3: 0.20 g (yield=16%).

1-2: Synthesis of the Trioxane 4

0.46 g (1.2 mmol) of trioxane 3 is solubilized in 3 ml of ethyl acetate. 0.7 ml of a 3M solution of HCl in ethyl acetate is added dropwise, at ambient temperature, to this mixture. The mixture is left stirring overnight. 50 ml of ether are added and the precipitate is filtered off. The powder is washed with 20 ml of ether and dried under vacuum for 2 h. A white powder is obtained that is identified as being the compound 4: 0.28 g (yield=70%).

1-3: Synthesis of the 7-chloro-4-(β-hydroxyethylamino)quinoline 5

A mixture of 4,7-dichloroquinoline (50.0 g, 252 mmol) and of 2-aminoethanol (46.26 g, 757 mmol) is heated, with magnetic stirring, at 150° C. for 15 min and then at 185° C. for 30 min. After returning to ambient temperature, the solid is suspended in 250 ml of a 10%, w/v, aqueous sodium hydroxide solution. The precipitate obtained is filtered off through sintered glass, washed with water and then brought to reflux in 125 ml of methanol for 15 min. After returning to ambient temperature, the precipitate is filtered off through sintered glass, washed with 3 times 40 ml of methanol and then dried under vacuum. The product 5 is obtained in the form of a white powder: 52.28 g (yield=93%).

1-4: Synthesis of the 7-chloro-4-(β-bromoethylamino)quinoline 6

Hydrobromic acid (22.5 ml, 414 mmol) and then sulphuric acid (7.5 ml, 140 mmol) are added dropwise onto the 7-chloro-4-(β-hydroxyethylamino)quinoline 5 (15 g, 67 mmol), the reaction medium being refrigerated using a bath of cold water. The reaction medium is then heated at 165° C. for 3 h 30 min, and then poured into 300 ml of cold water. The pH is then adjusted by adding $NaHCO_3$ (pH approximately 9) and the medium is then extracted at the reflux of toluene (300 ml) for 15 min. The organic phase is then collected and the product 6 is obtained by crystallization at −18° C. overnight, filtration, and then drying under vacuum: 10.55 g (yield=55%).

1-5: Synthesis of PA 1010

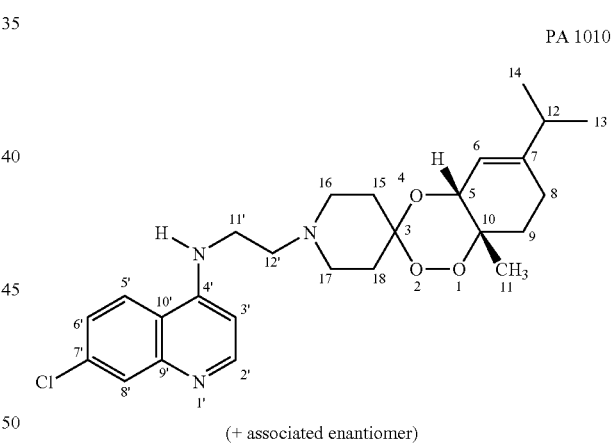

PA 1010

(+ associated enantiomer)

0.14 g (0.46 mmol) of trioxane 4 and 0.13 g (0.46 mmol) of the compound 6 are solubilized in 10 ml of DMF. 0.14 ml (1 mmol) of triethylamine is added to the mixture obtained and the mixture is left at ambient temperature for 96 h, with stirring. 50 ml of water are then added and the compound is extracted with 3×100 ml of ether. The solvents of the organic phase are evaporated off and the crude is then purified by chromatography column ($SiO_2$ 60 $ACC_{6-35}$ µm, eluent: 99/1, v/v, ether/triethylamine). The exiting of the products from the column is controlled by TLC ($SiO_2$ 60 F 254, visualized under UV). When the compound 6 no longer appears, the eluent phase is modified (80/20, v/v, dichloromethane/triethylamine) and the coupling product is recovered. The solvents of the phases containing the coupling product are evaporated off, and the crude is solubilized in 100 ml of ether and washed with 5 ml of water. The organic phase is dried by adding Na$_2$SO$_4$, filtered and evaporated. The oil obtained is solubilized in a minimum of dichloromethane, to which the same amount of n-hexane is added, and then evaporated under vacuum for 24 h, giving a white powder identified as being PA 1010: 0.08 g (yield=35%). Mp (melting point): 134-135° C. (decomposition). $^1$H NMR (300 MHz, 298 K, CDCl$_3$) δ, ppm: 8.55 (d, J=5.1 Hz, 1H, HC2'), 7.97 (d, J=2.1 Hz, 1H, HC8'), 7.66 (d, J=9.0 Hz, 1H, HC5'), 7.40 (dd, J=9.0 Hz, J=2.1 Hz, 1H, HC6'), 6.38 (d, J=5.4 Hz, 1H, HC3'), 6.01 (m, 1H, NH), 5.45 (d, J=4.8 Hz, 1H, HC6), 4.06 (broad s, 1H, HC5), 3.32 (td, J=5.1 Hz, J=5.4 Hz, 2H, HC11'), 2.81 (t, J=6.0 Hz, 2H, HC12'), 2.73-2.46 (m, 4H+1H, H-piperidone+HC9), 2.29-2.22 (m, 1H+2H, HC12+HC8), 2.10-1.76 (m, 4H, H-piperidone), 1.54-1.52 (m, 1H, HC9), 1.13 (broad s, 3H, HC11), 1.06 (d, J=4.8 Hz, 3H, HC13), HC14), 1.04 (d, J=4.8 Hz, 3H, HC13, HC14). $^{13}$C NMR (100 MHz, 293 K, CDCl$_3$) δ, ppm: 152.58 (C2'), 150.58 (C7), 150.09 (C4'), 149.39 (C9'), 135.26 (C7'), 129.13 (C8'), 125.84 (C6'), 121.60 (C5'), 117.66 (C10'), 116.36 (C6), 101.31 (C3), 99.71 (C3'), 79.18 (C10), 67.60 (C5), 55.25 (C12'), 49.94, 49.62 (C15, C16, C17, C18), 39.36 (C11'), 35.50 (C15, C16, C17, C18), 35.03 (C12), 26.59 (C8), 25.68 (C9), 21.86, 21.56 (C13, C14), 19.76 (C11). MS (DCI/NH$_3$>0) m/z (%): 472 (MH$^+$, 100)). Elemental analysis: for C$_{26}$H$_{34}$N$_3$O$_3$Cl.0.5H$_2$O: % theor. C 64.92, H 7.33, N 8.73; % exper. C 64.53, H 7.52, N 8.41.

2—Synthesis of PA 1011, Racemic Mixture

7-Chloro-N-{2-[6-isopropyl-8a-methyl-4a,7,8,8a-tetrahydro-1'H-spiro[1,2,4-benzotrioxine-3,4'-piperidin]-1'-yl]propyl}quinolin-4-amine

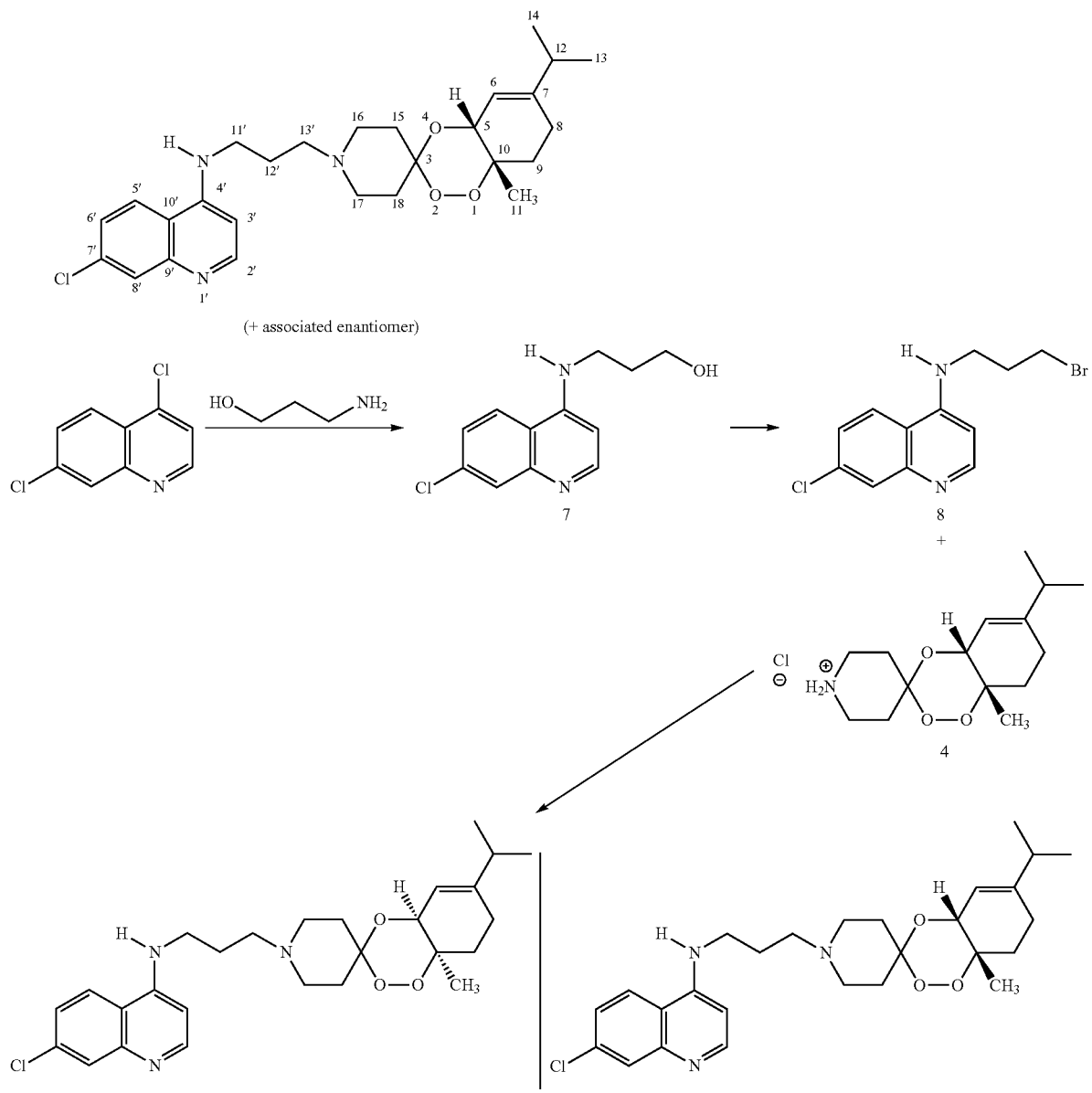

PA 1011

(+ associated enantiomer)

PA 1011

0.10 g (0.33 mmol) of trioxane 4 and 0.10 g (0.33 mmol) of compound 8 (4-(3-bromopropylamino)-7-chloroquine, prepared according to the method described by J. Lhomme et al., J. Med. Chem. 1977, 20, 106-113) are solubilized in 10 ml of DMF. The procedure is then carried out as described in Examples 1-5 above, using 0.10 ml (0.74 mmol) of triethylamine. A white powder is obtained, identified as being PA 1011: 0.05 g (yield=33%). Mp: 140-141° C. (decomp.). $^1$H NMR (300 MHz, 298 K, CDCl$_3$) δ, ppm: 8.52 (d, J=5.4 Hz, 1H, HC2'), 7.95 (d, J=2.1 Hz, 1H, HC8'), 7.77 (d, J=9.0 Hz, 1H, HC5'), 7.56 (m, 1H, NH), 7.39 (dd, J=9.0 Hz, J=2.1 Hz, 1H, HC6'), 6.34 (d, J=5.4 Hz, 1H, HC3'), 5.50 (d, J=4.8 Hz, 1H, HC6), 4.08 (broad s, 1H, HC5), 3.40 (td, J=4.8 Hz, J=4.8 Hz, 2H, HC11'), 2.74 (m, 2H, HC12'), 2.66 (t, J=5.4 Hz, 2H, HC13'), 2.34-1.71 (m, 8H+2H+1H, H-piperidone+HC8+HC9), 1.58-1.54 (m, 1H, HC9), 1.20-1.09 (broad s, 3H, HC11), 1.08 (d, J=6.6 Hz, 3H, HC13, HC14), 1.06 (d, J=6.6 Hz, 3H, HC13, HC14). MS (DCI/NH$_3$>0) m/z (%): 486 (MH$^+$, 100)). Elemental analysis: for C$_{27}$H$_{36}$N$_3$O$_3$Cl.0.5H$_2$O: % theor. C 65.50, H 7.53, N 8.48; % exper. C 65.78, H 7.36, N 8.12.

3—Synthesis of PA 1025, Achiral Molecule, and its Salts PA 1047 and PA 1042

7-Chloro-N-[1,2,5-trioxa-9-azaspiro[5.5]undec-9-yl)ethyl]quinolin-4-amine 3-1: Synthesis of the 3-methyl-3-[(triethylsilyl)dioxy]butanol 9

The procedure is carried out according to the method described by P. M. O'Neill et al. (Tetrahedron Letters, 42, 2001, 4569-4571).

3-2: Synthesis of PA 1023

10.72 g (48 mmol) of 3-methyl-3-[(triethylsilyl)dioxy]butanol 9 and 29.05 g (145 mmol) of N-(butoxycarbonyl)-4-piperidone 2 are solubilized in 250 ml of chloroform. 6.47 g (34 mmol) of para-toluenesulphonic acid are added at ambient temperature under argon, and the mixture is left stirring for 30 minutes. The reaction medium is then directly purified by chromatography (SiO$_2$ 60 ACC 70-200 μm, eluent: 20/80, v/v, ether/pentane). The exiting of the products from the column is controlled by TLC (SiO$_2$ 60 F 254, visualized with sulphuric acid). The solvents of the phases containing the product are evaporated off, giving a white solid identified as being PA 1023: 4.03 g (yield=30%). Mp: 69-70° C.

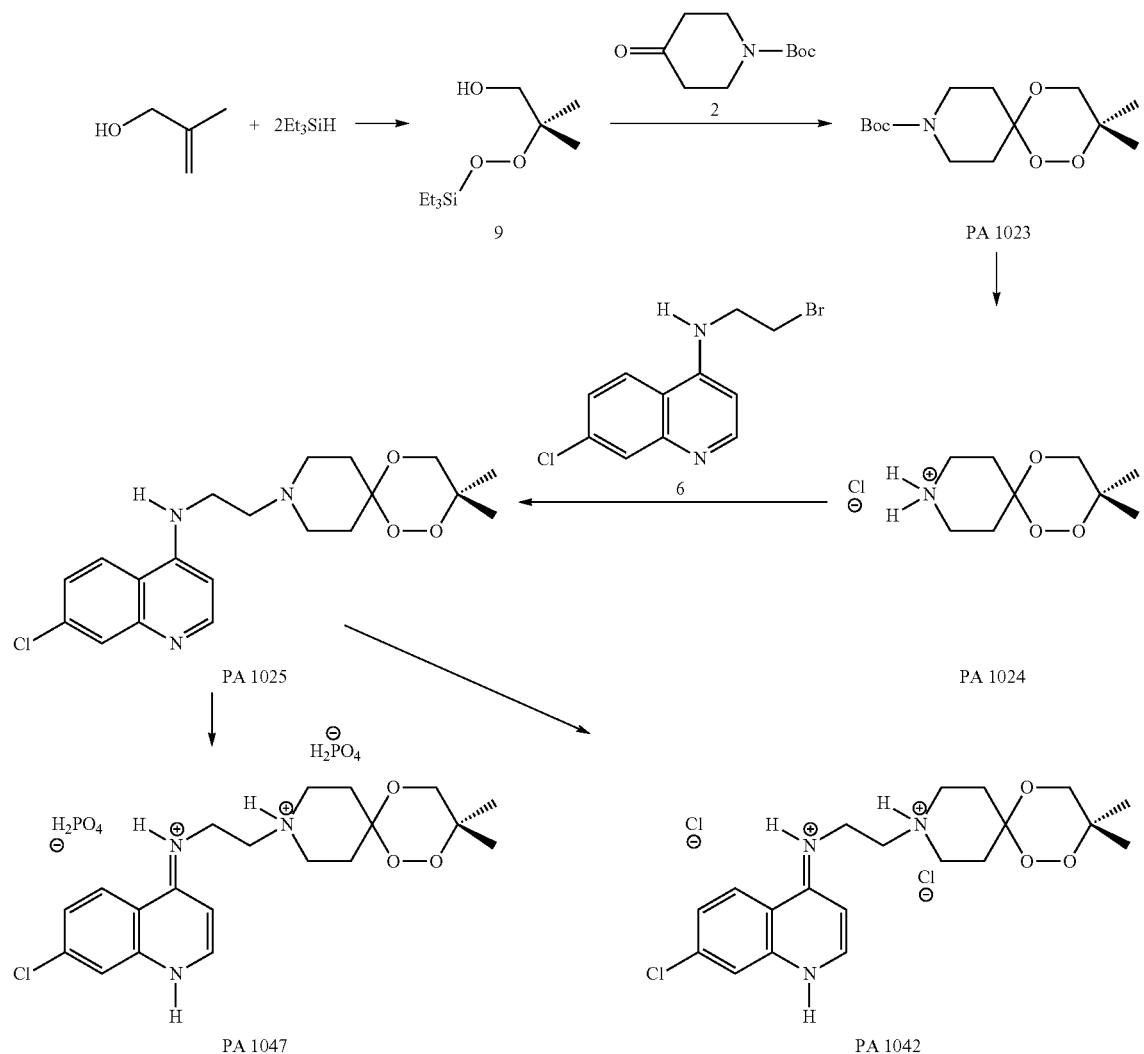

3-3: Synthesis of PA 1024

0.27 g (0.94 mmol) of PA 1023 is solubilized in 3 ml of ethyl acetate. 0.5 ml of a 3 M solution of HCl in ethyl acetate is added dropwise to this mixture, at ambient temperature. The mixture is then left stirring for 1 h. The solvents are then evaporated to ⅘ths under vacuum and 30 ml of ether are added. The precipitate that has appeared is filtered, washed with 20 ml of ether and dried under vacuum for 2 h. A white powder is obtained, identified as being PA 1024: 0.12 g (yield=56%). Mp: 155° C. (decomp.).

3-4: Synthesis of PA 1025

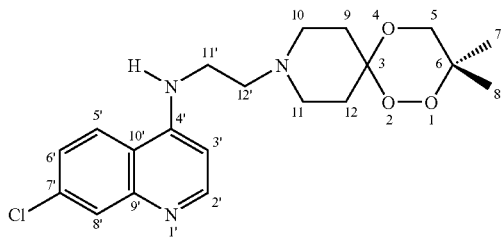
PA1025

0.47 g (2.11 mmol) of PA 1024 and 0.60 g (2.11 mmol) of compound 6 are solubilized in 25 ml of DMF. 0.65 ml (4.6 mmol) of triethylamine is added to the mixture obtained, and the mixture is left at ambient temperature for 72 h, with stirring. The DMF is evaporated off under vacuum and the residue is purified by chromatography column (SiO₂ 60 ACC 70-200 µm, eluent: 80/19/1, v/v/v, ether/methanol/triethylamine). The exiting of the products from the column is controlled by TLC (SiO₂ 60 F 254). The solvents of the phases containing the coupling product are evaporated off, and the crude is solubilized in 300 ml of ether and washed with 100 ml of water. The organic phase is dried by adding Na₂SO₄, filtered, and evaporated under vacuum for 24 h, giving a white powder identified as being PA 1025: 0.25 g (yield=30%). Mp: 156° C. (decomp.). $^1$H NMR (400 MHz, 233 K, CDCl₃) δ, ppm: 8.54 (d, J=5.2 Hz, 1H, HC2'), 7.93 (d, J=2.0 Hz, 1H, HC8'), 7.68 (d, J=8.8 Hz, 1H, HC5'), 7.40 (d, J=7.6 Hz, HC6'), 6.38 (d, J=5.6 Hz, 1H, HC3'), 6.15 (s, 1H, HN), 3.91 (broad s, 1H, HC5), 3.49, (d, J=11.6 Hz, 1H, HC5), 3.31 (s, 2H, HC11'), 3.12-1.60 (m, 8H, H-piperidone), 2.82 (s, 2H, HC12'), 1.55 (s, 3H, HC7, HC8), 1.14 (s, 3H, HC7, HC8). $^{13}$C NMR (100 MHz, 233 K, CDCl₃) δ, ppm: 152.70 (C2'), 150.05 (C4'), 149.15 (C9'), 135.26 (C7'), 128.94 (C8'), 125.91 (C6'), 121.91 (C5'), 117.54 (C10'), 100.82 (C3), 99.78 (C3'), 77.87 (C6), 67.15 (C5), 55.15 (C12'), 49.83 and 49.51 (C9, C12), 35.23 (C11'), 28.80 (C10, C11), 23.36, 22.33 (C7, C8). MS (DCI/NH₃>0) m/z (%): 392 (MH+100). Elemental analysis: for C₂₀H₂₆N₃O₃Cl: % theor. C 61.30, H 6.69, N 10.72; % exper. C 61.31, H 6.59, N 10.44.

3-5: Synthesis of PA 1042

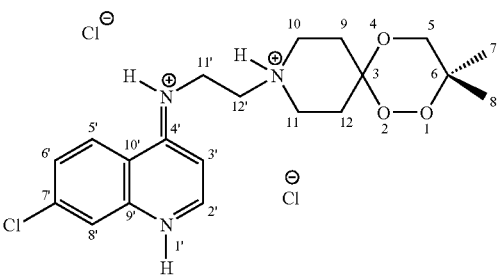
PA 1042

0.18 ml of 12 M hydrochloric acid is diluted in 2 ml of acetone. This solution is poured dropwise into a solution of 0.40 g (1.01 mmol) of PA 1025 in 18 ml of acetone. The suspension obtained is poured into 200 ml of ether with stirring. The mixture is filtered, and the precipitate is washed with 100 ml of ether and then dried under vacuum, giving a white powder identified as being PA 1042: 0.44 g (yield=95%). Mp: 174° C. (decomp.). $^1$H NMR (300 MHz, 298 K, DMSOd₆) δ, ppm: 14.61 (s, 1H, HN), 11.41 (s, 1H, HN), 9.76 (s, 1H, HN), 8.82 (d, J=9.0 Hz, HC5'), 8.66 (d, J=6.9 Hz, HC2'), 8.13 (s, 1H, HC8'), 7.79 (dd, J=9.0 Hz, J=1.8 Hz, 1H, HC6'), 7.05 (d, J=7.2 Hz, HC3'), 4.02 (m, 2H, HC11'), 3.80-3.40 (m, 2H+2H+2H, HC5+HC12'+H-piperidone), 3.07 (m, 3H, H-piperidone), 2.08 (m, 3H, H-piperidone), 1.37-1.06 (m, 6H, HC7, HC8). MS (ES/MS>0, MeOH) m/z (%): 392.25 (MH⁺, 100). Elemental analysis: for C₂₀H₂₆N₃O₃Cl.2HCl.1.4H₂O: % theor. C 49.02, H 6.33, N 8.57; % exper. C 48.73, H 5.93, N 8.50.

3-6: Synthesis of PA 1047

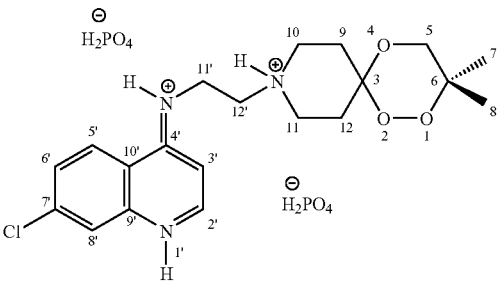
PA 1047

The procedure described in 3-5 above is carried out, using 0.14 ml of 15 M phosphoric acid diluted in 2 ml of acetone. 0.54 g of PA 1047 is obtained (yield=90%). Mp: 173° C. (decomp.). $^1$H NMR (300 MHz, 298 K, DMSOd₆) δ, ppm: 8.98 (m, 6H, HN+H₂PO₄), 8.44 (m, 2H, HC2'+HC5'), 7.87 (s, 1H, HC8'), 7.58 (d, J=7.2 Hz, 1H, HC6'), 6.72 (d, J=7.2 Hz, HC3'), 3.70-3.50 (m, 4H, HC11'+HC5), 2.89 (s, 2H, HC12'), 2.72 (s, 4H, H-piperidone), 2.26-1.76 (m, 4H, H-piperidone), 1.36-0.93 (m, 6H, HC7, HC8). MS (DCI/NH₃>0) M/Z (%): 392 (MH⁺, 9).

4—Synthesis of PA 1128, Achiral Molecule

N-(7-Chloroquinolin-4-yl)-N'-[2-(3,3-dimethyl-1,2,5-trioxa-9-azaspiro[5.5]undec-9-yl)ethyl]ethane-1,2-diamine

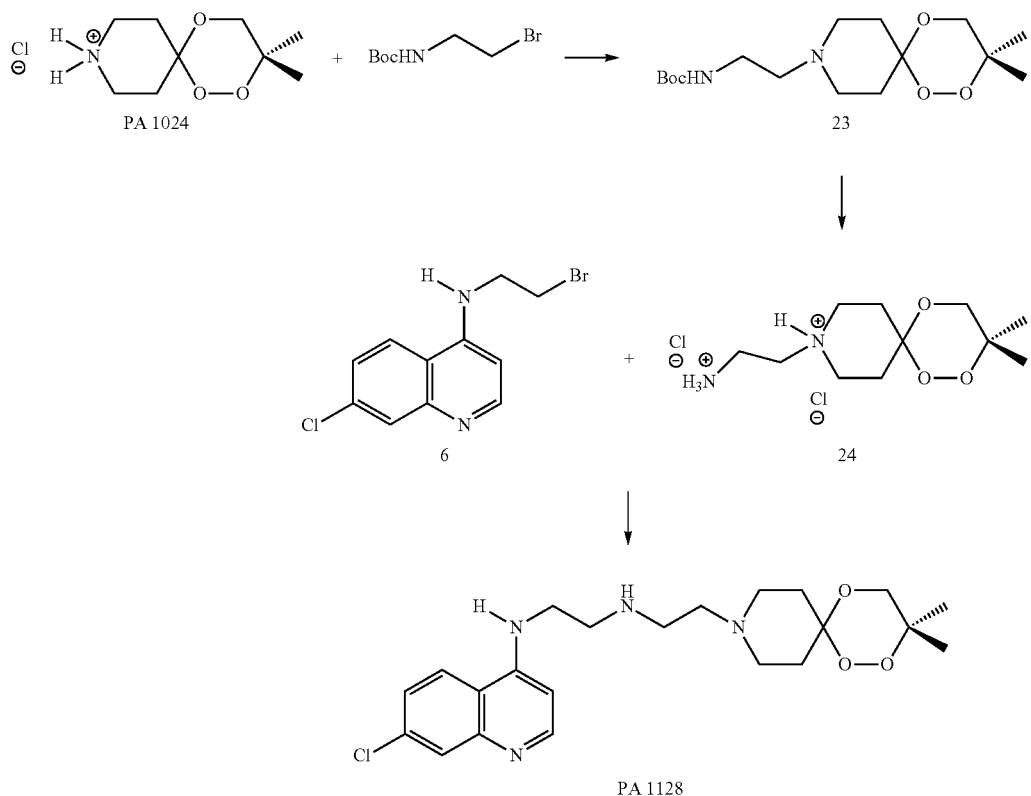

4-1: Synthesis of the [2-(3,3-dimethyl-1,2,5-trioxa-9-azaspiro[5.5]undec-9-yl)ethyl]carbamic acid tert-butyl ester 23

0.50 g (2.23 mmol) of PA 1024 and 0.50 g (2.23 mmol) of 2-(boc-amino)ethyl bromide are solubilized in 40 ml of DMF. 0.69 ml (4.91 mmol) of triethylamine are added to the mixture obtained and the mixture is left at ambient temperature for 72 h, with stirring. The DMF is evaporated off and the residue is then purified by chromatography column (SiO$_2$ 60 ACC 70-200 µm, eluent: ethyl acetate/MeOH/triethylamine (90/9/1, v/v/v)). The solvents of the phases containing the coupling product are evaporated off, and the residue is then taken up in 50 ml of ether and washed with 50 ml of water. The organic phase is dried by adding Na$_2$SO$_4$, filtered, and evaporated under vacuum, giving a white powder identified as being the product 23: 0.21 g (yield=28%).

4-2: Synthesis of the Compound 24

0.21 g (0.63 mmol) of compound 23 is solubilized in 4 ml of ethyl acetate and 3 ml of methanol. 5 ml of a 3M solution of HCl in ethyl acetate are added dropwise to this mixture, at ambient temperature. The mixture is left stirring for 24 h. The solvents are then evaporated to ⅘$^{ths}$ under vacuum and 30 ml of ether are added. The precipitate which has appeared is filtered off, washed with 20 ml of ether and dried under vacuum for 2 h. A white powder is obtained that is identified as being the compound 24: 0.17 g (yield=quantitative).

4-3: Synthesis of PA 1128

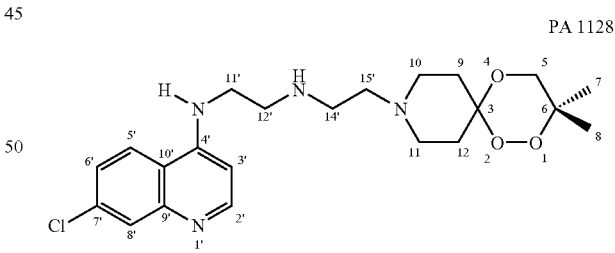

0.10 g (0.31 mmol) of 24 and 0.89 g (0.31 mmol) of 6 are solubilized in 5 ml of DMF. 0.14 ml (1.02 mmol) of triethylamine are added to the mixture obtained, and the mixture is left at ambient temperature for 72 h, with stirring. The DMF is evaporated off and the residue is then purified by chromatography column (SiO$_2$ 60 ACC 70-200 µm, eluent: CH$_2$Cl$_2$/MeOH/triethylamine (24.9/75/0.1, v/v/v)). The solvents of the phases containing the coupling product are evaporated off, and the residue is then taken up in 50 ml of ether and washed with 50 ml of water. The organic phase is dried by adding Na₂SO₄, filtered, and evaporated under vacuum, giving an oil identified as being PA 1128: 0.004 g (yield=3%). ¹H NMR (300 MHz, 298 K, CDCl₃) δ, ppm: 8.53 (d, J=5.4 Hz, 1H, HC2'), 7.96 (d, J=2.1 Hz, 1H, HC8'), 7.78 (d, J=9.0 Hz, 1H, HC5'), 7.38 (dd, J=9.0 Hz, J=2.2 Hz, HC6'), 6.39 (d, J=5.4 Hz, 1H, HC3'), 6.01 (s, 1H, NH), 3.75 (broad s, 1H, HC5), 3.45 (m, 1H+2H, HC5+HC11'), 3.07 (t, J=6.3 Hz, HC12'), 2.77 (m, 2H, HC14'), 2.56 (m, 2H+2H, HC15'+H-piperidone), 2.45 (m, 2H, H-piperidone), 1.79 (m, 4H, H-piperidone), 1.50 (s, 3H, HC7, HC8), 1.12 (s, 3H, HC7, HC8). MS (DCI/NH₃>0) m/z (%): 435 (MH⁺, 5).

5—Synthesis of PA 1102, Achiral Molecule

N-[3-(3,3-Dimethyl-1,2,5-trioxa-9-azaspiro[5.5]undec-9-yl)-3-oxopropyl]-6-methoxyquinolin-8-amine

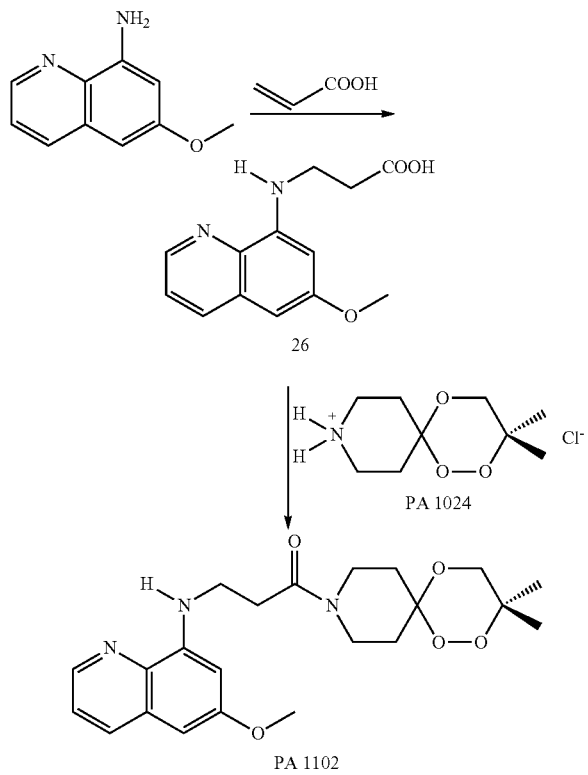

5-1: Synthesis of the 3-(6-methoxyquinolin-8-ylamino) propionic acid 26

A mixture of 5.0 g (19.56 mmol) of 6-methoxy-8-aminoquinoline hydrobromide, 1.48 ml (21.51 mmol) of acrylic acid and 5.45 ml (39.12 mmol) of triethylamine is dissolved in 25 ml of toluene and brought to 110° C. for 16 h, with magnetic stirring. 10 ml of a 10% (w/v) aqueous sodium hydroxide solution are then added and the reaction medium is kept at 100° C. for 20 min, with stirring. After returning to ambient temperature, the phase containing the toluene is eliminated and the aqueous phase is extracted with 100 ml of chloroform. The aqueous phase is then acidified by adding acetic acid until a pH of 5-6 is obtained. The precipitate obtained is filtered off and then washed with water. After drying under vacuum, the compound 26 is obtained in the form of a green powder: 1.77 g (yield=37%).

5-2: Synthesis of PA 1102

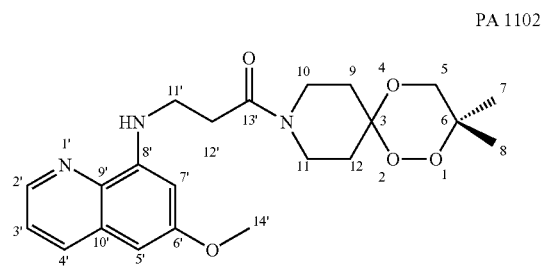

0.50 g (2.23 mmol) of PA 1024 and 0.55 g (2.23 mmol) of compound 26 are dissolved in 20 ml of DMF. 1.23 ml (11.17 mmol) of N-methylmorpholine and 1.16 g (2.23 mmol) of PYBOP® (benzotriazol-1-yloxytrispyrrolidinophosphonium hexafluorophosphate) are added successively to the mixture obtained. The mixture is left at ambient temperature for 24 h, with stirring. After the addition of 80 ml of dichloromethane, the organic phase is washed with 300 ml of a saturated NaHCO₃ solution and then with twice 300 ml of water. The solvents of the organic phase are evaporated off under vacuum, giving an oil. The residue is then purified by chromatography column (SiO₂ 60 ACC 70-200 µm, eluent: ethyl acetate/triethylamine (90/10, v/v)). The phases containing the coupling product are combined and then washed with 1 l of water. The organic phase is dried by adding Na₂SO₄, filtered, and evaporated under vacuum, giving a white powder identified as being PA 1102: 0.63 g (yield=71%). Mp: 138° C. (decomp.). ¹H NMR (300 MHz, 298 K, CDCl₃): δ, ppm: 8.55 (d, J=4.2 Hz, 1H, HC2'), 7.94 (dd, J=8.1 Hz, J=2.1 Hz, 1H, HC4'), 7.32 (dd, J=8.1 Hz, J=4.2 Hz, HC3'), 6.42 (m, 1H, HN), 6.38 (m, 1H+1H, HC5'+HC7'), 3.91 (s, 3H, HC14'), 3.67 (q, J=5.7 Hz, HC11'), 3.65 (m, 1H, HC5), 3.57-3.35 (m, 1H+4H, HC5+H-piperidone), 2.77 (t, J=6.6 Hz, 2H, HC12'), 2.34 (m, 1H, H-piperidone), 2.06 (m, 3H, H-piperidone), 1.49 (s, 3H, HC7, HC8), 1.13 (s, 3H, HC7, HC8). MS (DCI/NH₃>0) m/z (%): 416 (MH⁺, 62). Elemental analysis: for C₂₂H₂₉N₃O₅: % theor. C 63.60, H 7.04, N 10.11; % exper. C 63.63, H 6.76, N 10.11.

6—Synthesis of PA 1035, Achiral Molecule

7-Trifluoromethyl-N-[1,2,5-trioxa-9-azaspiro[5.5]undec-9-yl)ethyl]quinolin-4-amine

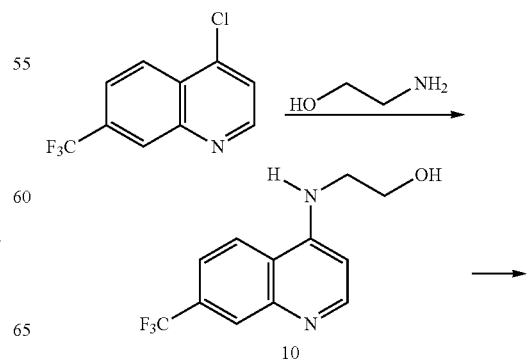

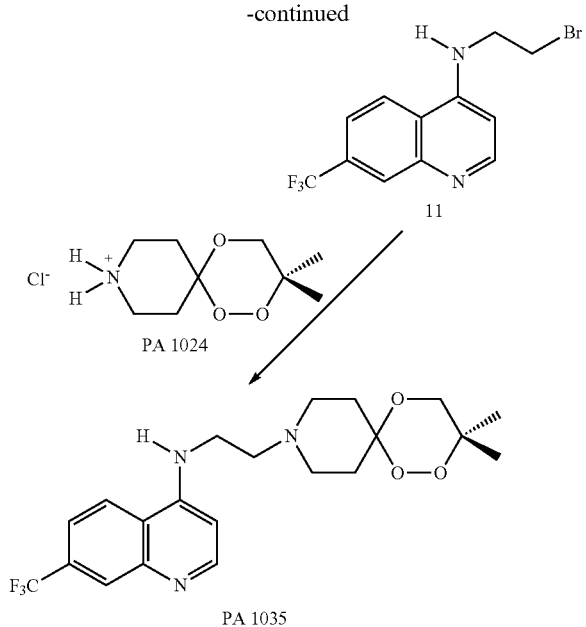

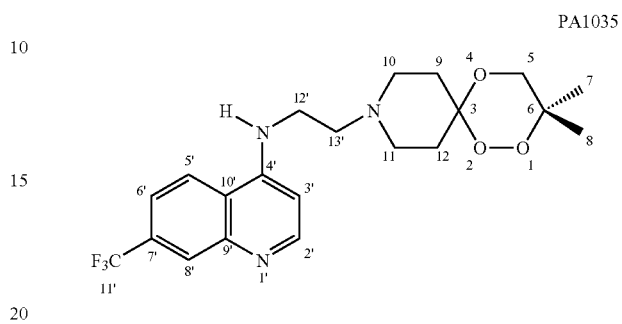

6-1: Synthesis of the 7-trifluoromethyl-4-(β-hydroxyethylamino)quinoline 10

A mixture of 4-chloro-7-(trifluoromethyl)quinoline (1.0 g, 4.7 mmol) and of 2-aminoethanol (0.86 g, 14.1 mmol) is heated, with magnetic stirring, at 150° C. for 15 min and then 185° C. for 30 min. After returning to ambient temperature, the solid is suspended in 5 ml of a 10%, w/v, aqueous sodium hydroxide solution. The precipitate obtained is filtered off through sintered glass, washed with water and then brought to reflux in 10 ml of ethanol for 15 min. After returning to ambient temperature, water is added until a precipitate appears. The precipitate is filtered off through sintered glass, washed with 10 ml of water and then dried under vacuum. The product 10 is obtained in the form of a white powder: 0.82 g (yield=68%). Mp: 181-182° C.

6-2: Synthesis of the 7-trifluoromethyl-4-(β-bromoethylamino)quinoline 11

Hydrobromic acid (0.88 ml, 16.2 mmol) and then sulphuric acid (0.29 ml, 5.5 mmol) are added dropwise to the 7-trifluoromethyl-4-(β-hydroxyethylamino)quinoline 10 (0.67 g, 2.6 mmol), the reaction medium being refrigerated using a bath of cold water. The reaction medium is then heated at 165° C. for 3 h 30 min, and then poured into 10 ml of cold water. The pH is then adjusted by adding $NaHCO_3$ (pH approximately 9) and the medium is then extracted at the reflux of toluene (10 ml) for 15 min. The organic phase is then collected and the product 11 is obtained by crystallization at −18° C. overnight, filtration, and then drying under vacuum: 0.48 g (yield=58%). Mp: 106° C. (decomp.).

6-3: Synthesis of PA 1035

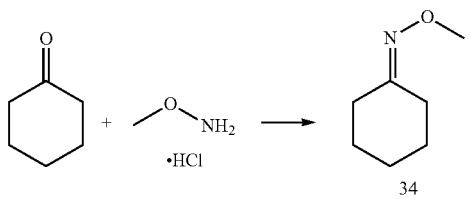

0.18 g (0.8 mmol) of PA 1024 and 0.24 g (0.7 mmol) of the compound 11 are solubilized in 5 ml of acetonitrile. 0.34 g (3.2 mmol) of $Na_2CO_3$ is added to the mixture obtained, and the mixture is left at ambient temperature for 45 min, with stirring. The mixture is then heated at 40° C. for 45 min, at 50° C. for 45 min, at 60° C. for 45 min, and at 70° C. for 1 h 30 min. The reaction mixture is then filtered, the solvents are evaporated off and the residue is purified by chromatography column ($SiO_2$ 60 ACC 70-200 μm, eluent: 80/20, v/v, dichloromethane/triethylamine). The exiting of the products from the column is controlled by TLC ($SiO_2$ 60 F 254). The solvents of the phases containing the coupling product are evaporated off, and the crude is solubilized in 50 ml of ether and washed with 10 ml of water. The organic phase is dried by adding $Na_2SO_4$, filtered, and evaporated under vacuum for 24 h, giving a white powder identified as being PA 1035: 0.46 g (yield=13%). $^1$H NMR (300 MHz, 298 K, $CDCl_3$) δ, ppm: 8.63 (d, J=5.1 Hz, 1H, HC2'), 8.30 (s, 1H, HC8'), 7.92 (d, J=8.7 Hz, 1H, HC5'), 7.64 (dd, J=8.7 Hz, J=1.5 Hz, HC6'), 6.48 (d, J=5.4 Hz, 1H, HC3'), 6.23 (s, 1H, HN), 3.79 (broad s, 1H, HC5), 3.59 (broad s, 1H, HC5), 3.38 (s, 2H, HC12'), 2.87 (t, J=5.7 Hz, 2H, HC13'), 2.74-1.90 (m, 8H, H-piperidone), 1.37 (s, 3H, HC7, HC8), 1.04 (s, 3H, HC7, HC8); Mp: 154° C. (decomp.); MS ($DCI/NH_3$>0) m/z (%): 426 ($MH^+$, 100%).

7—Synthesis of PA 1020, Achiral Molecule

7-Chloro-N-[2-(7,14,15-trioxa-3-azadispiro[5.1.5.2]pentadec-3-yl)ethyl]quinolin-4-amine

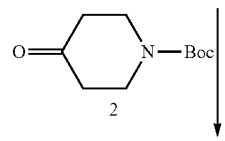

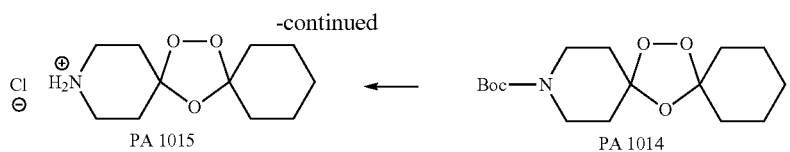

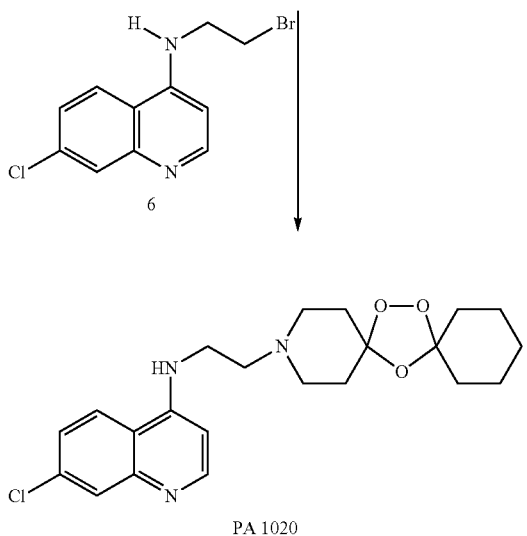

7-1: General Procedure for Preparing the 1,2,4-trioxolanes

An ozone generator (Trailigaz® LI, 1981) is used to generate ozone from oxygen. The ketone O-methyloxime derivative and the N-Boc-piperidone 2 are dissolved in a 20/80, v/v, dichloromethane/pentane mixture and then placed at 0° C. The reaction medium is first of all purged by bubbling with oxygen for 5 minutes, and then subjected to bubbling with ozone for 10 minutes (flow rate: 200 l/h, power: 0.6 A). The solution is then purged for 5 minutes by bubbling with oxygen and then 10 minutes by bubbling with argon. The reaction crude is then concentrated at 28° C. using a rotary evaporator. The oil thus obtained is then chromatographed on a silica column.

7-2: Synthesis of the Trioxolane PA 1014

A solution of cyclohexanone O-methyloxime 34 (0.636 g, 5 mmol), prepared according to the method described by Donaruma et al., J. Org. Chem., 1957, 22, 1024, and of the compound 2 (1.99 g, 10 mmol) in a dichloromethane (20 ml)/pentane (80 ml) mixture is treated by bubbling with ozone according to the general procedure detailed in 7-1 above. The reaction crude obtained is then chromatographed on a silica column (SiO$_2$ 60 AAC 6-35 μm, eluents: 65/35, v/v, hexane/ether). The PA 1014 is obtained, after recrystallization from 15 ml of an ethanol/water (2/1, v/v) mixture, in the form of a white powder: 0.22 g (yield=14%).

7-3: Synthesis of the Trioxolane PA 1015

The PA 1014 (0.610 g, 1.95 mmol) is dissolved in 3 ml of ethyl acetate and then 12 M hydrochloric acid (290 μl, 3.48 mmol), diluted beforehand in 870 μl of ethyl acetate, is poured in. The mixture is kept at ambient temperature for 17 h, with magnetic stirring. The product is then precipitated by adding 25 ml of diethyl ether, and then filtered through sintered glass. After washing with ether and drying under vacuum, the product PA 1015 is obtained in the form of a white powder: 0.25 g (yield=51%).

7-4: Synthesis of PA 1020

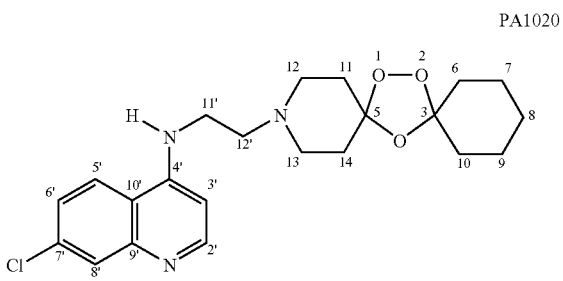

The PA 1015 (0.18 g, 0.73 mmol) and the compound 6 (0.21 g, 0.73 mmol) are suspended in 5 ml of dimethylformamide and then 226 μl (1.62 mmol) of triethylamine are added dropwise. The medium is kept at ambient temperature for 89 h, with magnetic stirring. After the addition of 70 ml of water, the aqueous phase is extracted with 100 ml of diethyl ether, and then saturated with NaCl and extracted twice with 100 ml of ether. The ethereal phases are combined, dried with Na$_2$SO$_4$, concentrated on a rotary evaporator, and then chromatographed on silica (SiO$_2$ 60 AAC 6-35 μm, eluents: ether/triethylamine (9.9/0.1, v/v)). The phases containing the PA 1020 are combined and the solvents are then evaporated off, giving a white powder: 0.09 g (yield=29%). Mp: 153° C. (decomp.). $^1$H NMR (400 MHz, 298 K, CDCl$_3$) δ, ppm: 8.53 (d, J=5.6 Hz, 1H, HC2'), 7.99 (d, J=1.5 Hz, 1H, HC8'), 7.68 (d, J=6.9 Hz, 1H, HC5'), 7.40 (dd, J=5.6 Hz and J=1.5 Hz, 1H, HC6'), 6.39 (d, J=5.6 Hz, 1H, HC3'), 6.10 (broad s, 1H, HN), 3.33 (m, 2H, HC11'), 2.82 (t, 2H, HC12'), 2.72 and 2.57 (2m, 2H and 2H, HC12 and HC13), 1.94 (m, 4H, HC11+HC14), 1.81-1.57 (m, 14H, HC6+HC7+HC9+HC10), 1.47 (m, 1H, HC8), 1.40 (m, 1H, HC8). $^{13}$C NMR (100 MHz, 298 K, CDCl$_3$) δ, ppm: 152.02 (C2'), 150.33 (C4'), 148.92 (C9'), 135.54 (C7'), 128.77 (C8'), 125.97 (C6'), 121.55 (C5'), 117.59 (C10'), 109.93 (C3), 107.20 (C5), 99.64 (C3'), 55.29 (C12'), 51.04 (C12, C13), 39.57 (C11'), 34.83 (C11, C14), 34.96 and 24.19 (C6, C7, C9, C10), 25.24 (C8). MS (ES/MS>0) m/z (%): 418.25 (MH+). Elemental analysis: for C$_{22}$H$_{28}$ClN$_3$O$_3$: % theor. C 63.22, H 6.75, N 10.05; % exper. C 63.26, H 6.74, N 9.76.

The purity of the compound was determined by HPLC according to the following conditions: Beckman Coulter ODS C18 column, 5 μm, 4.6×250 mm; eluents: A: H$_2$O 0.1% TFA, B: 90/10 CH$_3$CN/H$_2$O 0.1% TFA, gradient: from 10% to 100% of B in 40 min, then 100% of B for 20 min. Flow rate: 1 ml/min. μ=254 nm. Injected volume: 10 μl. Sample at 1 mg/ml in methanol. Purity: 98%.

8—Synthesis of PA 1021, Achiral Molecule, and its Salt PA 1040

7-Chloro-N-[2-(1H-dispiro[piperidine-4,3'-[1,2,4] trioxolane-5',2''-tricyclo[3.3.1.1$^{3,7}$]decan]-1-yl)ethyl] quinolin-4-amine 8-1: Synthesis of the 2-adamantanone O-methyloxime 35

3.76 g (45 mmol) of methoxylamine, in hydrochloride form, and 4.36 g (55.1 mmol) of pyridine are added to 4.51 g (30 mmol) of 2-adamantanone in 30 ml of methanol. The reaction medium is stirred at ambient temperature for 66 h, the solvents are evaporated off under vacuum, and the residue is then diluted with 50 ml of dichloromethane and 50 ml of water. The organic phase is separated and the aqueous phase is then extracted again with 30 ml of dichloromethane. The organic phases are combined, washed with two times 30 ml of dilute hydrochloric acid (1 M) and 30 ml of brine, and then dried over magnesium sulphate. After filtration and evaporation in a rotary evaporator, the product 35 is obtained in the form of a white powder: 3.57 g (yield=66%).

8-2: Synthesis of the Trioxolane PA 1016

The compound is synthesized according to the procedure described in U.S. Pat. No. 6,486,199 (Vennerstrom et al.). A solution of 2-adamantanone O-methyloxime 35 (0.9 g, 5 mmol) and of 2 (1.99 g, 10 mmol) in a dichloromethane (20 ml)/pentane (80 ml) mixture is treated by bubbling with ozone according to the general procedure described in 7-1 above. The reaction crude obtained is then chromatographed using a silica column (SiO$_2$ 60 AAC 6-35 μm, eluents: 80/20, v/v, hexane/ether). The N-Boc-trioxolane PA 1016 is

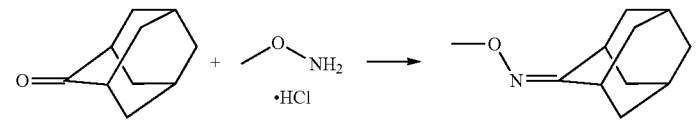

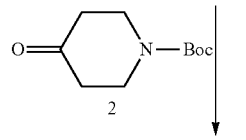

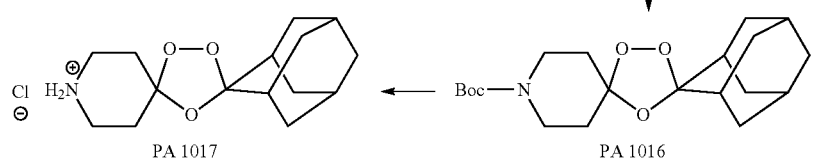

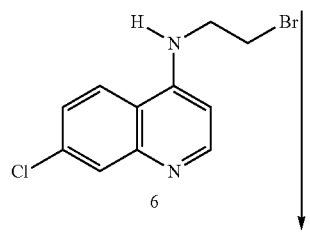

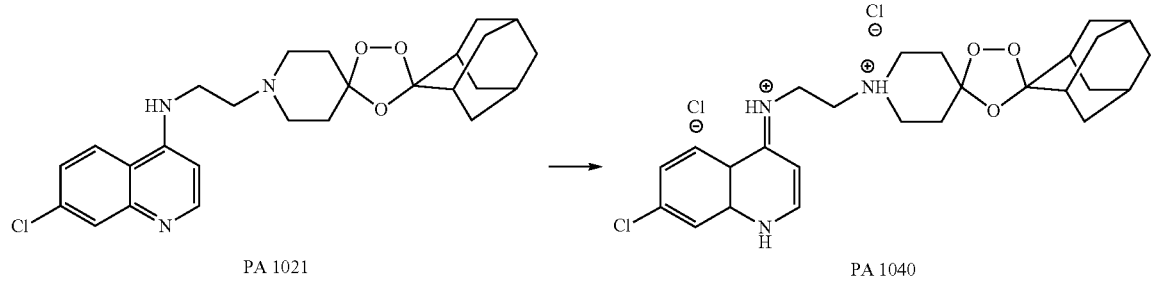

obtained, after recrystallization from 15 ml of ethanol/water (2/1, v/v), in the form of a white powder: 0.37 g (yield=21%).

8-3: Synthesis of the Trioxolane PA 1017

266 μl (3.20 mmol) of 12 M hydrochloric acid, diluted beforehand in 800 μl of ethyl acetate, are added to 0.65 g (1.78 mmol) of PA 1016 in 3 ml of ethyl acetate. The mixture is kept at ambient temperature for 20 h, with stirring. The product is then precipitated by adding 25 ml of diethyl ether, and then filtered through sintered glass. After washing with ether and drying under vacuum, the product PA 1017 is obtained in the form of a white powder: 0.42 g (yield=78%).

8-4: Synthesis of PA 1021

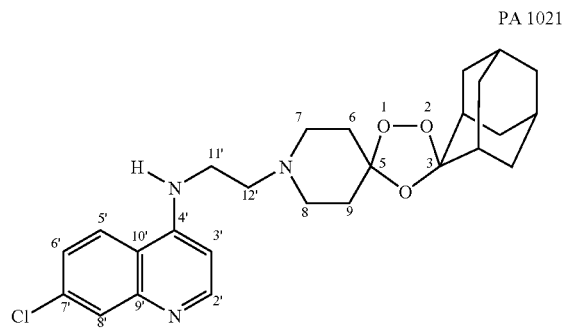

PA 1021

The PA 1017 (0.32 g, 1.06 mmol) and the compound 6 (0.30 g, 1.06 mmol) are suspended in 10 ml of dimethylformamide, and 326 μl (2.33 mmol) of triethylamine are then added dropwise. The medium is kept at ambient temperature for 112 h, with magnetic stirring. After the addition of 100 ml of water, the aqueous phase is extracted with 100 ml of diethyl ether and then saturated with NaCl and extracted with 2 times 100 ml of ether. The ethereal phases are combined, dried with $Na_2SO_4$, concentrated on a rotary evaporator and then chromatographed on silica ($SiO_2$ 60 AAC 6-35 μm, eluents: 97/3, v/v, ethyl acetate/triethylamine). The phases containing the PA 1021 are combined and the solvents are then evaporated off, giving a white powder: 0.25 g (yield=52%). Mp: 130° C. $^1$H NMR (400 MHz, 298 K, $CDCl_3$) δ, ppm: 8.53 (d, J=5.6 Hz, 1H, HC2'), 7.98 (d, J=1.5 Hz, 1H, HC8'), 7.69 (d, J=6.9 Hz, 1H, HC5'), 7.40 (dd, J=5.6 Hz and J=1.5 Hz, 1H, HC6'), 6.38 (d, J=5.6 Hz, 1H, HC3'), 6.10 (broad s, 1H, HN), 3.33 (m, 2H, HC11'), 2.82 (m, 2H, HC12'), 2.73 and 2.57 (2m, 2H and 2H, HC7 and HC8), 1.94 (m, 2H+2H, HC6+HC9), 2.04-1.70 (m, 14H, H-adamantane). $^{13}$C NMR (100 MHz, 298 K, $CDCl_3$) δ, ppm: 152.95 (C2'), 150.30 (C4'), 149.00 (C9'), 135.49 (C7'), 128.81 (C8'), 125.95 (C6'), 121.57 (C5'), 117.60 (C10'), 112.34 (C3), 107.27 (C5), 99.64 (C3'), 55.32 (C12'), 51.12 (C7, C8), 39.56 (C11'), 34.95 (C6, C9), 37.11, 36.76, 35.24, 35.15, 27.21, 26.81 (C-adamantane). MS (ES/MS>0, MeOH) m/z (%): 470.05 (MH+, 38). Elemental analysis: for $C_{26}H_{32}ClN_3O_3$: % theor. C 66.44, H 6.86, N 8.94; % exper. C 66.66, H 6.75, N 8.60. Purity: 98% (determined by HPLC according to the protocol described above in 7-4).

8-5: Synthesis of PA 1040

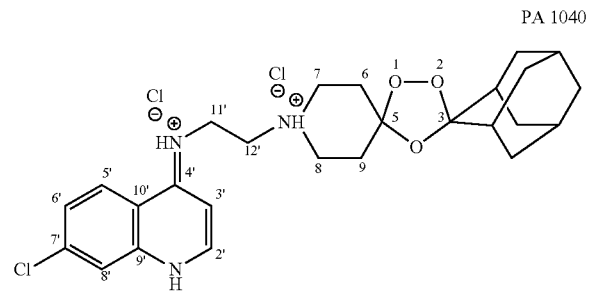

PA 1040

500 μl (0.50 mmol) of 1 M hydrochloric acid in ether are added to 0.11 g (0.24 mmol) of PA 1021 dissolved in 2.5 ml of chloroform. After the addition of 15 ml of ether, the suspension is centrifuged and the pellet obtained is then successively washed with ether (twice at 15 ml) and then with 15 ml of pentane. After drying under vacuum, the product PA 1040 is obtained in the form of a white powder: 0.13 g (yield=98%). Mp: 189° C. (decomp.). $^1$H NMR (300 MHz, 298 K, $DMSOd_6$) δ, ppm: 14.60 (broad s, 1H, HNC4'), 11.50 (broad s, 1H, HNC14'), 9.76 (broad s, 1H, HNC2'), 8.81 (d, J=9.3 Hz, 1H, HC5'), 8.66 (d, J=6.9 Hz, 1H, HC2'), 8.13 (d, J=1.8 Hz, 1H, HC8'), 7.79 (dd, J=9.3 Hz and J=1.8 Hz, 1H, HC6'), 7.05 (d, J=6.9 Hz, 1H, HC3'), 4.04 (broad s, 2H, HC11'), 3.67-3.15 (m, 2H+2H, HC7+HC8), 3.41 (broad s, 2H, HC12'), 2.50-1.66 (m, 2H+2H+14H, HC6+HC9+H-adamantane). MS (ES/MS>0, MeOH) m/z (%): 470.15 (MH+). Elemental analysis: for $C_{26}H_{32}ClN_3O_3.2HCl.3H_2O$: % theor. C 52.29, H 6.75, N 7.03; % exper. C 52.22, H 6.68, N 7.10.

9—Synthesis of PA 1026, Achiral Molecule $N^4$-[2-(1H-Dispiro[piperidine-4,3,-[1,2,4]trioxolane-5',2"-tricyclo[3.3.1.1$^{3,7}$]decan]-1-yl)ethyl]-$N^6$,$N^6$-dimethylquinoline-4,6-diamine

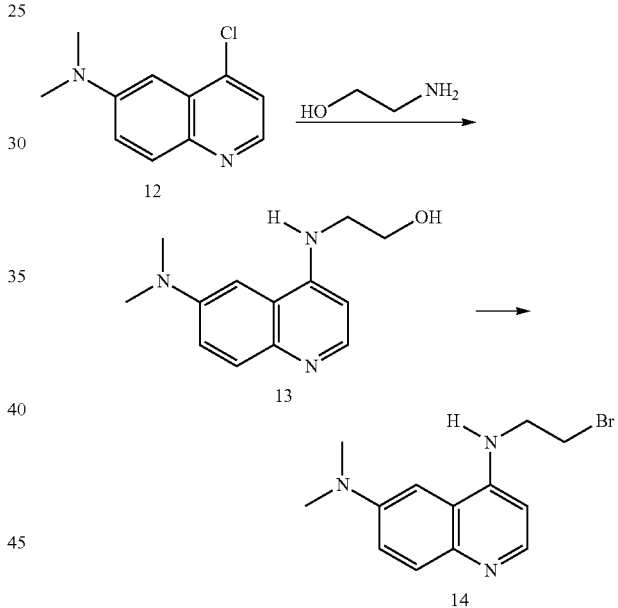

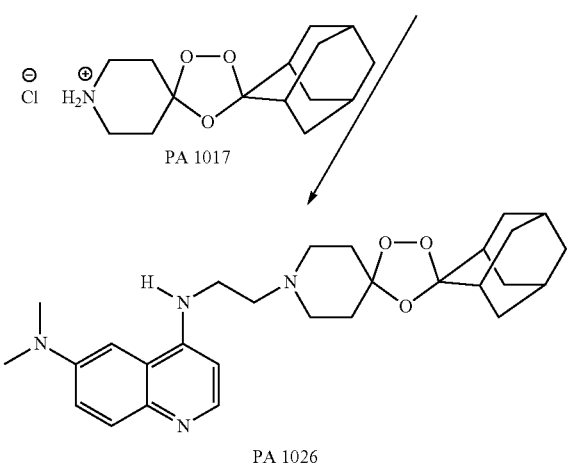

PA 1026

9-1: Synthesis of the 6-dimethylamino-4-(β-hydroxyethylamino)quinoline 13

A mixture of 4-chloro-6-dimethylaminoquinoline 12 (4.92 g, 24 mmol), prepared according to the method described by Riegel et al., J. Am. Chem. Soc., 1946, 68, 1264, and of 2-aminoethanol (43.99 g, 720 mmol) is heated, with magnetic stirring, at 150° C. for 15 min and then at 185° C. for 30 min. After returning to ambient temperature, the solid is suspended in 25 ml of a 10%, w/v, aqueous sodium hydroxide solution and 165 ml of water. The precipitate obtained is filtered through sintered glass, washed with water and then dried under vacuum. The product is obtained in the form of a white powder: 4.86 g (yield=88%).

9-2: Synthesis of the 6-dimethylamino-4-(β-bromoethylamino)quinoline 14

Hydrobromic acid (6.6 ml, 122 mmol) and then sulphuric acid (2.2 ml, 41.4 mmol) are added dropwise to the 6-dimethylamino-4-(β-hydroxyethylamino)quinoline 13 (4.56 g, 19.7 mmol), the reaction medium being refrigerated using a bath of cold water. The reaction medium is then heated at 165° C. for 3 h 30 min and then poured into 71 ml of cold water. The pH is then adjusted by adding $NaHCO_3$ (pH approximately 9) and the medium is then extracted at the reflux of toluene (71 ml) for 15 min. The organic phase is then collected and the product is obtained by crystallization at −18° C. overnight, filtration, and then washing with hexane and drying under vacuum: 3.28 g (yield=57%).

9-3: Synthesis of PA 1026

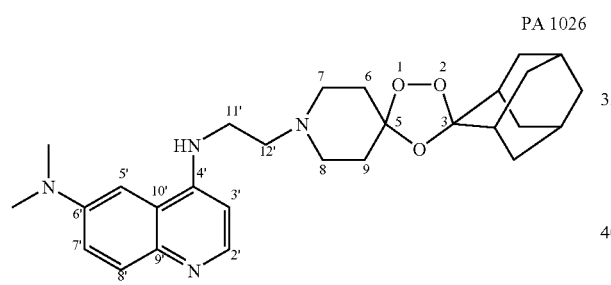

0.30 g (0.99 mmol) of PA 1017 and 0.29 g (0.99 mmol) of 6-dimethylamino-4-(β-bromoethylamino)quinoline 14 are suspended in 10 ml of dimethylformamide, and then 305 μl (2.18 mmol) of triethylamine are added dropwise. The medium is kept at ambient temperature for 113 h, with magnetic stirring. After the addition of 100 ml of water, the aqueous phase is extracted with 100 ml of diethyl ether, then saturated with NaCl and extracted with twice 100 ml of ether. The ethereal phases are combined, dried with $Na_2SO_4$, concentrated in a rotary evaporator and then chromatographed on silica ($SiO_2$ 60 AAC 6-35 μm, eluents: dichloromethane/triethylamine (9/1, v/v)). The exiting of the product is monitored by TLC ($SiO_2$ 60 F 254). After precipitation with dichloromethane/hexane, the product PA 1026 is obtained in the form of a white powder: 0.14 g (yield=30%). $^1$H NMR (300 MHz, 298 K, $CDCl_3$) δ, ppm: 8.36 (d, J=5.1 Hz, 1H, HC2'), 7.96 (d, J=9.3 Hz, 1H, HC8'), 7.32 (dd, J=9.3 Hz and J=2.4 Hz, 1H, HC7'), 6.66 (d, J=2.4 Hz, 1H, HC5'), 6.36 (d, J=5.1 Hz, 1H, HC3'), 5.99 (broad s, 1H, HN), 3.35 (m, 2H, HC11'), 2.85 (m, 2H, HC12'), 2.69 and 2.63 (2m, 2H and 2H, HC7 and HC8), 2.04-1.71 (m, 2H+2H+14H, HC6+HC9+H-adamantane). MS (ES/MS>0, MeOH) m/z (%): 479.45 (MH$^+$). Elemental analysis: for $C_{28}H_{38}N_4O_3 \cdot H_2O$: % theor. C 67.71, H 8.12, N 11.28; % exper. C 67.78, H 8.02, N 11.13. Purity: 99% (determined by HPLC according to the protocol described in 7-4 above).

10—Synthesis of PA 1069, Achiral Molecule

7-Chloro-N-{2-[2-(1H-dispiro[piperidine-4,3'-[1,2,4]trioxolane-5',2''-tricyclo[3.3.1.1$^{3,7}$]decan]-1-yl)ethoxy]ethyl}quinolin-4-amine

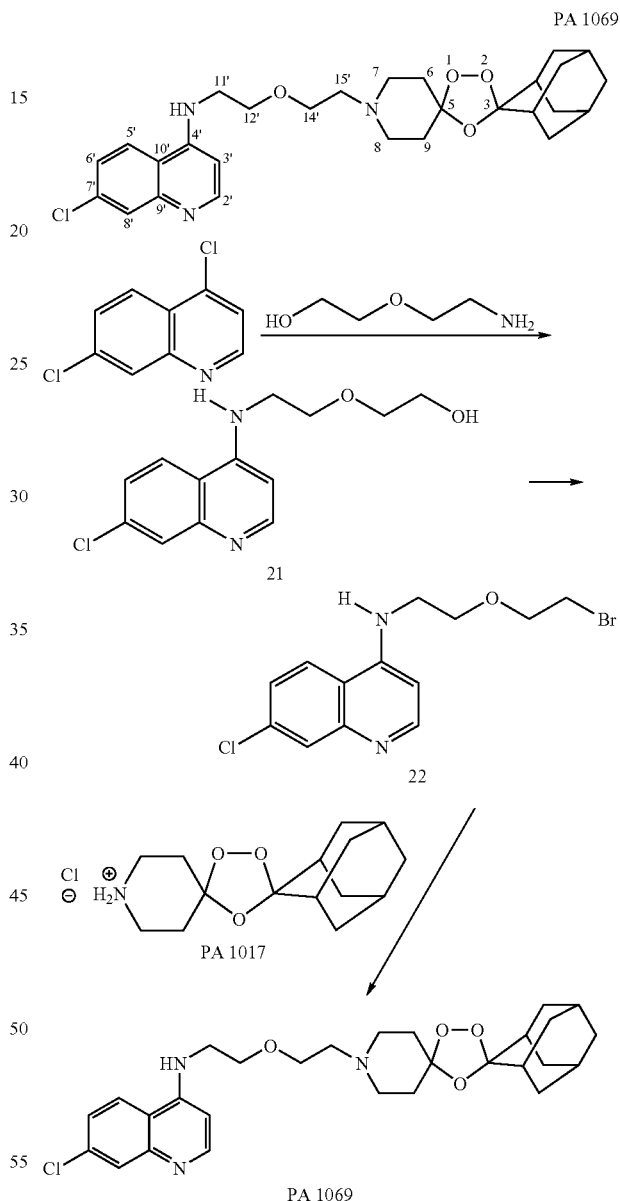

10-1: Synthesis of the 2-[2-(7-chloroquinolin-4-ylamino)ethoxy]ethanol 21

A mixture of 4,7-dichloroquinoline (5.0 g, 25.0 mmol) and of 2-(2-aminoethoxy)ethanol (10.51 g, 100.0 mmol) is heated at 135° C. for 5 h, with magnetic stirring. After cooling, the reaction medium is taken up in 200 ml of diethyl ether and the stirring is maintained overnight at ambient temperature. The solid residue formed is isolated, and then dissolved in a mixture of 500 ml of dichloromethane/triethylamine (9/1, v/v)

and filtered through sintered glass containing a bed of silica (SiO₂ 60 AAC 70-200 μm). The product is then eluted from the silica with ethanol (2 l). The ethanolic phases are combined and evaporated. 50 ml of dichloromethane are added to the residue and the organic phase is washed with twice 50 ml of water. The organic phase is recovered, dried over Na₂SO₄, and then evaporated in a rotary evaporator. After drying under vacuum, the compound 21 is obtained in the form of a beige powder: 5.03 g (yield=75%).

10-2: Synthesis of the [2-(2-bromoethoxy)ethyl]-(7-chloroquinolin-4-yl)amine 22

Hydrobromic acid (5.9 ml, 109.1 mmol) and then sulphuric acid (2.0 ml, 37.0 mmol) are added dropwise to 4.7 g of compound 21 (17.6 mmol), the reaction medium being refrigerated using a bath of cold water. The reaction medium is then heated at 155° C. for 2 h 30 min, and then poured into 70 ml of cold water. The pH is then adjusted by adding NaHCO₃ (pH approximately 9), and the medium is then extracted at the reflux of toluene (70 ml) for 20 min. The organic phase is then collected and the compound 22 is obtained after crystallization at −18° C. overnight, filtration, washing with hexane, and then drying under vacuum: 1.77 g (yield=31%).

10-3: Synthesis of PA 1069

0.50 g (1.66 mmol) of PA 1017 and 0.77 g (1.66 mmol) of compound 22 are dissolved in 25 ml of dimethylformamide and then 508 μl (3.64 mmol) of triethylamine are added dropwise. The medium is kept at ambient temperature for 101 h, with magnetic stirring. After the addition of 100 ml of dichloromethane, the organic phase is washed once with 200 ml of water saturated with NaHCO₃, and then 3 times with 200 ml of water. The organic phase is then dried with Na₂SO₄, concentrated in a rotary evaporator and then chromatographed on silica (SiO₂ 60 AAC 6-35 μm, eluents: ethyl acetate/triethylamine (90/10, v/v)). After recrystallization from dichloromethane/n-hexane and drying under vacuum, the product PA 1069 is obtained in the form of a white powder: 0.29 g (yield=35%). Mp: 144° C. (decomp.). ¹H NMR (300 MHz, 298 K, CDCl₃) δ, ppm:8.53 (d, J=5.4 Hz, 1H, HC2'), 7.99 (d, J=2.1 Hz, 1H, HC8'), 7.86 (d, J=9.0 Hz, 1H, HC5'), 7.44 (dd, J=9.0 Hz and J=2.1 Hz, 1H, HC6'), 6.42 (d, J=5.4 Hz, 1H, HC3'), 5.86 (broad s, 1H, HN), 3.83 (m, 2H, HC12'), 3.70 (m, 2H, HC14'), 3.51 (m, 2H, HC11'), 2.78-2.60 (m, 2H+2H+2H, HC15'+HC7+HC8), 2.05-1.70 (m, 2H+2H+ 14H, HC6+HC9+H-adamantane). MS (ES/MS>0, MeOH) m/z (%): 514.25 (MH⁺). Elemental analysis: for C₂₈H₃₆ClN₃O₄: % theor. C 65.42, H 7.06, N 8.17; % exper. C 65.32, H 7.02, N 8.08.

11—Synthesis of PA 1080, Achiral Molecule

N-{2-[(7-Chloroquinolin-4-yl)amino]ethyl}-1H-dispiro[piperidine-4,3'-[1,2,4]trioxolane-5',2''-tricyclo[3.3.1.1³,⁷]decane]-1-carboxamide

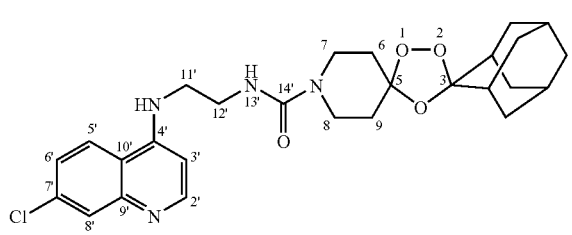

PA 1080

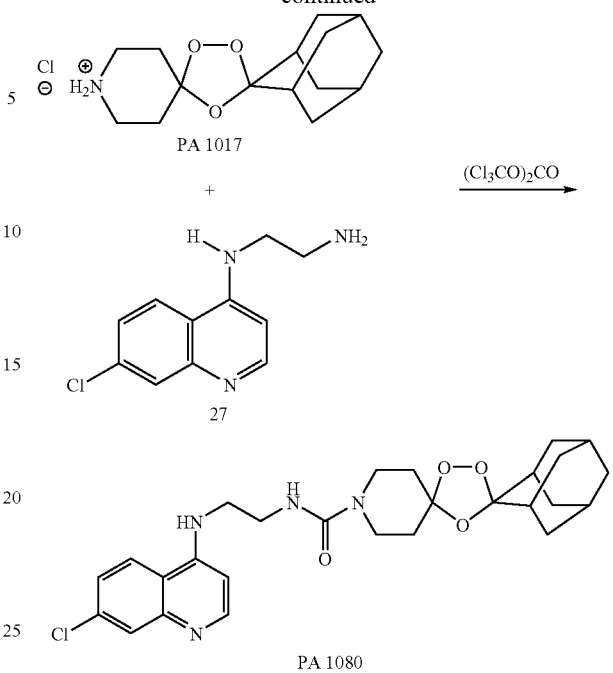

544 μl (3.87 mmol) of anhydrous triethylamine are added to 0.53 g (1.76 mmol) of PA 1017, dried beforehand under vacuum, in 15 ml of dry dichloromethane. This solution is then added dropwise to a solution of 0.19 g (0.65 mmol) of triphosgene in 5 ml of dry dichloromethane. The reaction medium is kept at ambient temperature for 1 h, with magnetic stirring. Moreover, 272 μl (1.94 mmol) of anhydrous triethylamine are added to a solution of 0.39 g (1.76 mmol) of 27 (prepared according to the method described by Meunier et al. in PCT International Application WO 01/77105) in 15 ml of dry dichloromethane. This solution is then transferred onto the initial reaction medium and the entire mixture is maintained at ambient temperature for 16 h, with magnetic stirring. After the addition of 100 ml of dichloromethane, the organic phase is washed with 200 ml of water saturated with NaHCO₃ and then with twice 200 ml of water. The organic phase is then dried with Na₂SO₄, concentrated, and then chromatographed on silica (SiO₂ 60 AAC 6-35 μm, eluents: dichloromethane/triethylamine (90/10, v/v)). After recrystallization with a dichloromethane/diethyl ether mixture, the compound obtained is taken up in 75 ml of chloroform. The organic phase is successively washed with 150 ml of water, 150 ml of brine, and with three times 150 ml of water. The organic phase is then dried with Na₂SO₄, concentrated in a rotary evaporator, and dried under vacuum. The product PA 1080 is obtained in the form of a white powder: 0.20 g (yield=23%). Mp: 192° C. (decomp.). ¹H NMR (250 MHz, 298 K, CDCl₃) δ, ppm: 8.41 (d, J=5.6 Hz, 1H, HC2'), 7.89 (d, J=2.0 Hz, 1H, HC8'), 7.86 (d, J=8.8 Hz, 1H, HC5'), 7.47 (broad s, 1H, HNC12'), 7.34 (dd, J=8.8 Hz and J=2.0 Hz, 1H, HC6'), 6.21 (d, J=5.6 Hz, 1H, HC3'), 5.30 (t, J=6.4 Hz, 1H, HNC13'), 3.69 and 3.32 (2m, 2H and 2H, HC11' and HC12'), 3.52 (m, 2H+2H, HC7+HC8), 1.93-1.66 (m, 2H+2H+14H, HC6+HC9+H-adamantane). MS (ES/MS>0, MeOH) m/z (%): 513.30 (MH⁺). Elemental analysis: for C₂₇H₃₃ClN₄O₄.0.7H₂O: % theor. C 61.69, H 6.59, N 10.66; % exper. C 61.69, H 6.09, N 10.35.

12—Synthesis of PA 1097, Achiral Molecule

2-[(7-Chloroquinolin-4-yl)amino]ethyl-1H-dispiro[piperidine-4,3'-[1,2,4]trioxolane-5',2"-tricyclo[3.3.1.1³,⁷]decane]-1-carboxylate

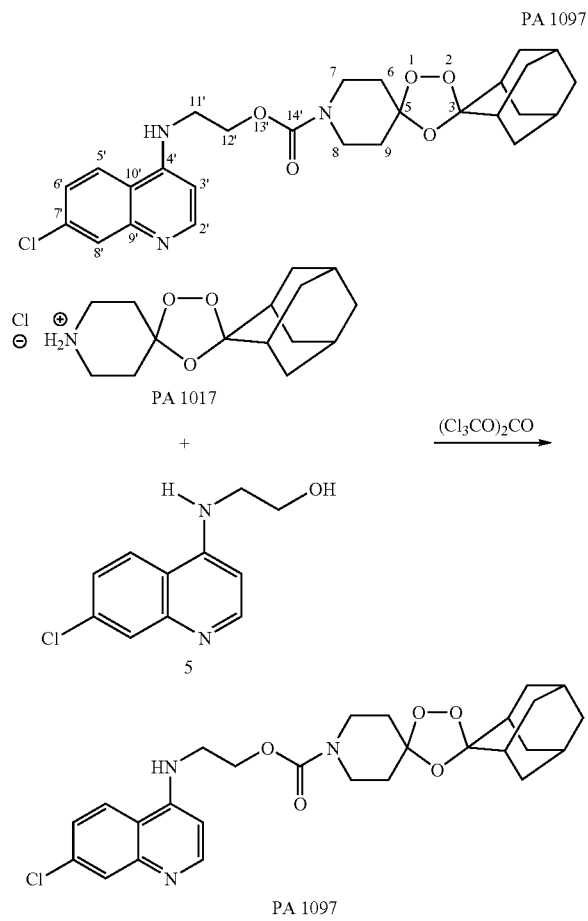

269 μl (1.92 mmol) of anhydrous triethylamine are added to 0.42 g (1.92 mmol) of compound 5 (dried under vacuum beforehand) in 15 ml of dry dichloromethane. The solution thus prepared is then added to 0.21 g (0.71 mmol) of triphosgene in 5 ml of dry dichloromethane. The reaction medium is kept at ambient temperature for 3 h 30 min, with magnetic stirring. Moreover, 594 μl (4.22 mmol) of anhydrous triethylamine are added to dry PA 1017 (0.58 g, 1.90 mmol) in 15 ml of dry dichloromethane. This solution is then transferred onto the initial reaction medium and the entire mixture is kept at ambient temperature for 1 h 45 min, with magnetic stirring. After the addition of 100 ml of dichloromethane, the organic phase is washed with 200 ml of water saturated with $NaHCO_3$ and then with twice 150 ml of water. The organic phase is then dried with $Na_2SO_4$, concentrated in a rotary evaporator, and then chromatographed on silica ($SiO_2$ 60 AAC 6-35 μm, eluents: ethyl acetate/triethylamine (90/10, v/v)). The fractions containing the product are combined, the solvents are evaporated off and 70 ml of chloroform are added. The organic phase is washed with twice 150 ml of water, and dried over $MgSO_4$. A volume of hexane is added, then the entire mixture is subsequently concentrated in a rotary evaporator and then dried under vacuum. The product PA 1097 is obtained in the form of a white powder: 0.07 g (yield=7%). Mp: 159° C. (decomp.). $^1$H NMR (300 MHz, 298 K, $CDCl_3$) δ, ppm: 8.55 (d, J=5.4 Hz, 1H, HC2'), 7.97 (d, J=2.1 Hz, 1H, HC8'), 7.72 (d, J=8.7 Hz, 1H, HC5'), 7.40 (dd, J=8.7 Hz, J=2.1 Hz, 1H, HC6'), 6.37 (d, J=5.4 Hz, 1H, HC3'), 6.31 (broad s, 1H, HN), 4.56 (m, 2H, HC12'), 3.60-3.52 (m, 2H+2H+2H, HC7+HC8+HC12'), 2.05-1.63 (m, 2H+2H+14H, HC6+HC9+H-adamantane). MS (DCI/$NH_3$>0) m/z (%): 514 ($MH^+$). Elemental analysis: for $C_{27}H_{32}ClN_3O_5.1H_2O$: % theor. C 60.95, H 6.44, N 7.90; % exper. C 60.88, H 5.75, N 7.73.

Besides the compounds for which details of the protocols for obtaining them have been given above, other compounds of formula (I) according to the invention are grouped together in the following table; these examples are not limiting and merely illustrate the present invention.

TABLE

| Compound | Melting point (° C.) | $^1$H NMR (δ, ppm) |
|---|---|---|
| PA1038 | 144 | 300 MHz, 298 K, $CDCl_3$: 8.52 (d, J=5.1 Hz, 1H), 7.95 (s, 1H), 7.76 (d, J=9.0 Hz, 1H), 7.57 (s, 1H), 7.37 (dd, J=8.7 Hz, J=1.8 Hz), 6.34 (d, J=5.1 Hz, 1H), 3.85 (broad s, 1H), 3.53 (broad s, 1H), 3.40 (m, 2H), 2.73-2.51 (m, 2H + 4H), 2.18-1.87 (m, 2H + 4H), 1.55 (s, 3H), 1.17 (s, 3H) |
| PA 1039 | 157 (decomp.) | 300 MHz, 298 K, $CDCl_3$: 8.38 (d, J=5.1 Hz, 1H), 7.88 (d, J=9.3 Hz, 1H), 7.31 (dd, J=2.7 Hz, J=9.3 Hz, 1H), 6.66 (s, 1H), 6.35 (d, J=5.1 Hz, 1H), 5.82 (s, 1H), 3.79 (broad s, 1H), 3.47 (broad s, 1H), 3.33 (q, J=5.4 Hz, 2H), 3.07 (s, 6H), 2.83 (t, J=5.4 Hz, 2H), 2.66-2.50 (m, 4H), 2.42-1.80 (m, 4H), 1.51 (s, 3H), 1.12 (s, 3H) |

TABLE-continued

| Compound | Melting point (° C.) | ¹H NMR (δ, ppm) |
|---|---|---|
| 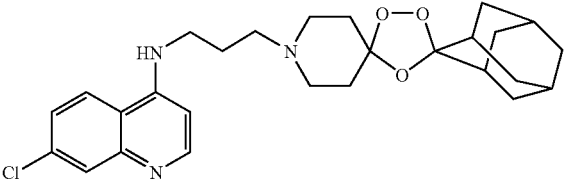 PA 1041 | 159 (decomp.) | 300 MHz, 298 K, CDCl₃: 8.50 (d, J=5.4 Hz, 1H), 7.99 (d, J=2.1 Hz, 1H), 7.78 (d, J=9.0 Hz, 1H), 7.60 (broad s, 1H), 7.38 (dd, J=9.0 Hz and J=2.1 Hz, 1H), 6.35 (d, J=5.4 Hz, 1H), 3.41 (m, 2H), 2.77-2.58 (m, 2H + 2H + 2H), 2.09-1.72 (m, 2H + 2H + 2H + 14H) |
| 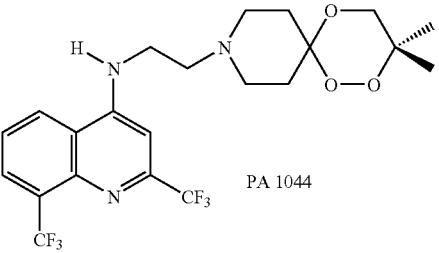 PA 1044 | 144 (decomp.) | 8.08 (d, J=7.5 Hz, 1H), 7.98 (d, J=8.4 Hz), 7.58 (dd, J=7.8 Hz, J=7.8 Hz, 1H), 6.75 (s, 1H), 6.40 (s, 1H), 3.81 (broad s, 1H), 3.49 (broad s, 1H), 3.39 (q, J=5.1 Hz, 2H), 2.86 (t, J=6.0 Hz, 2H), 2.71-2.52 (m, 4H), 2.18-1.70 (m, 4H), 1.52 (s, 3H), 1.14 (s, 3H) |
| 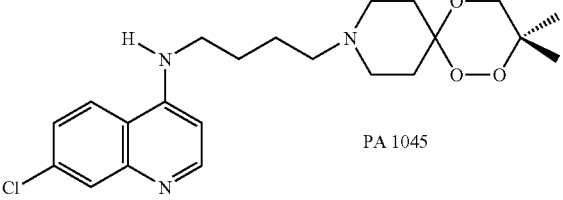 PA 1045 | 145 | 300 MHz, 298 K, CDCl₃: 8.54 (d, J=5.4 Hz, 1H), 7.96 (d, J=2.1 Hz, 1H), 7.67 (d, J=9.0 Hz, 1H), 7.37 (dd, J=9.0 Hz, J=2.4 Hz), 6.42 (d, J=5.4 Hz, 1H), 5.33 (s, 1H), 3.80 (broad s, 1H), 3.46 (broad s, 1H), 3.34 (q, J=6.3 Hz, 2H), 2.68-2.38 (m, 2H + 4H), 2.10-1.78 (m, 2H + 4H), 1.70 (q, J=6.9 Hz, 2H), 1.51 (s, 3H), 1.15 (s, 3H) |
| 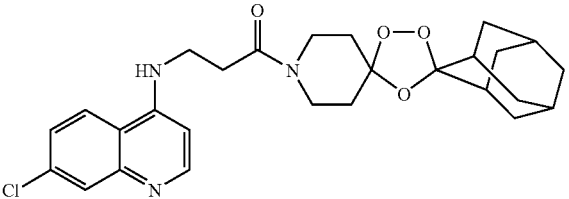 PA 1048 | 137 | 300 MHz, 298 K, CDCl₃: 8.49 (d, J=5.4 Hz, 1H), 7.97 (d, J=2.1 Hz, 1H), 7.76 (dd, J=9.0 Hz and J=2.1 Hz, 1H), 7.36 (d, J=9.0 Hz, 1H), 6.44 (d, J=5.4 Hz, 1H), 6.43 (broad s, 1H), 3.87 and 3.63 (2m, 1H and 1H), 3.70 (m, 2H), 3.54 (m, 1H + 1H), 2.76 (m, 2H), 2.00-1.70 (m, 2H + 2H + 14H) |
| 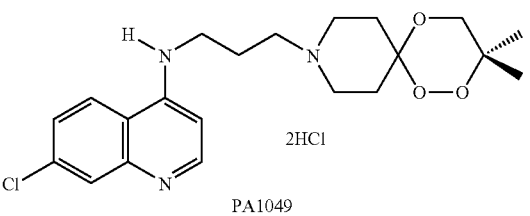 2HCl PA1049 | 142 (decomp.) | 300 MHz, 298 K, DMSOd₈: 14.30 (s, 1H), 11.20 (s, 1H), 9.71 (s, 1H), 8.73 (d, J=9.0 Hz), 8.59 (d, J=6.9 Hz), 8.08 (d, J=2.1 Hz, 1H), 7.79 (dd, J=9.3 Hz, J=2.1 Hz, 1H), 6.95 (d, J=6.9 Hz), 3.75 (m, 1H), 3.67-3.40 (m, 2H + 1H + 2H), 3.22 (m, 2H), 2.93 (m, 2H), 2.25-1.80 (m, 2H + 4H), 1.39-1.06 (m, 6H) |
| 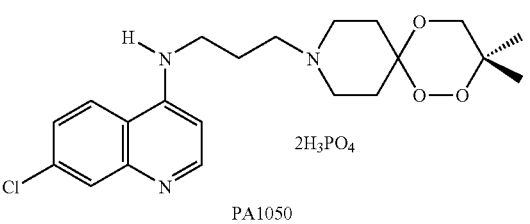 2H₃PO₄ PA1050 | 166 (decomp.) | 300 MHz, 298 K, D₂O: 8.22 (d, J=7.2 Hz, 1H), 8.02 (m, 1H), 7.73 (m, 1H), 7.53 (m, 1H), 6.72 (d, J=7.2 Hz, 1H), 3.80 (m, 1H), 3.70-3.40 (m, 2H + 1H + 2H), 3.23 (m, 2H), 3.13-2.97 (m, 2H), 2.19-1.87 (m, 2H + 4H), 1.43-1.05 (m, 6H) |

TABLE-continued

| Compound | Melting point (° C.) | ¹H NMR (δ, ppm) |
|---|---|---|
| 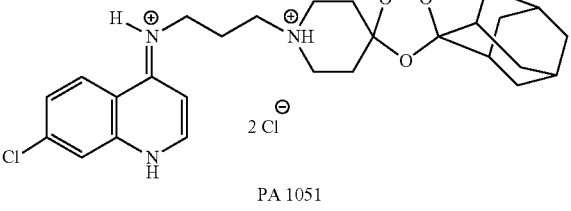 PA 1051 | 120 (decomp.) | 300 MHz, 298 K, DMSO-$d_6$: 14.25 (broad s, 1H), 11.39 (broad s, 1H), 9.63 (broad s, 1H), 8.70 (d, J=9.0 Hz, 1H), 8.59 (d, J=7.2 Hz, 1H), 8.06 (d, J=2.1 Hz, 1H), 7.78 (dd, J=9.0 Hz and J=2.1 Hz, 1H), 6.94 (d, J=7.2 Hz, 1H), 3.65 (broad s, 2H), 3.60-2.90 (m, 2H + 2H), 3.20 (broad s, 2H), 2.27-1.66 (m, 2H + 2H + 2H + 14H) |
| 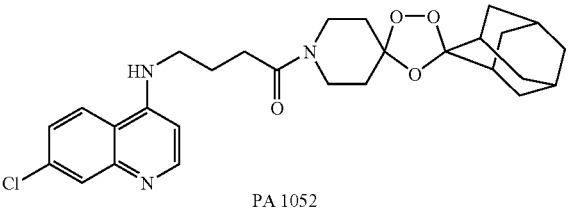 PA 1052 | 149 (decomp.) | 300 MHz, 298 K, CDCl$_3$: 8.48 (d, J=5.4 Hz, 1H), 7.96 (d, J=2.1 Hz, 1H), 7.85 (d, J=9.0 Hz, 1H), 7.37 (dd, J=9.0 Hz, J=2.1 Hz, 1H), 6.96 (broad s, 1H), 6.32 (d, J=5.4 Hz, 1H), 3.85 and 3.71 (2m, 1H and 1H), 3.55 (m, 1H + 1H), 3.33 (m, 2H), 2.61 (m, 2H), 2.20 (m, 2H), 2.00-1.70 (m, 2H + 2H + 14H) |
| 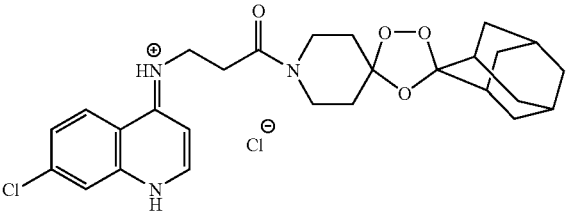 PA 1057 | 90 (decomp.) | 300 MHz, 298 K, DMSOd$_6$: 14.28 (broad s, 1H), 9.52 (broad s, 1H), 8.65 (d, J=9.0 Hz, 1H), 8.54 (d, J=7.2 Hz, 1H), 8.06 (d, J=2.1 Hz, 1H), 7.77 (dd, J=9.0 Hz, J=2.1 Hz, 1H), 6.90 (d, J=7.2 Hz, 1H), 3.76 (broad s, 2H), 3.64-3.44 (m, 4H), 1.91-1.65 (m, 2H + 2H + 14H) |
| 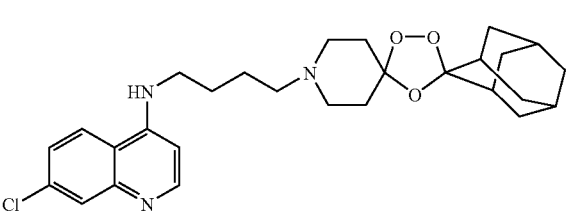 PA 1059 | 138 (decomp.) | 300 MHz, 298 K, CDCl$_3$: 8.54 (d, J=5.4 Hz, 1H), 7.97 (d, J=2.1 Hz, 1H), 7.68 (d, J=8.7 Hz, 1H), 7.37 (dd, J=8.7 Hz and J=2.1 Hz, 1H), 6.42 (d, J=5.4 Hz, 1H), 5.31 (broad s, 1H), 3.34 (m, 2H), 2.62 and 2.45 (2m, 2H and 4H), 2.05-1.69 (m, 2H + 2H + 2H + 2H + 14H) |
| 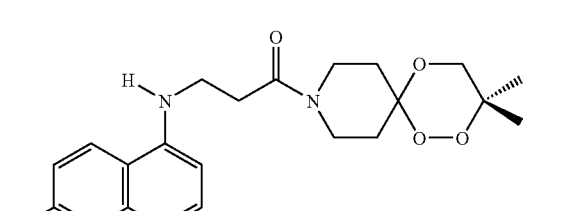 PA1060 | 184 (decomp.) | 300 MHz, 298 K, CDCl$_3$: 8.54 (d, J=5.4 Hz, 1H), 7.96 (d, J=2.1 Hz, 1H), 7.66 (d, J=9.0 Hz, 1H), 7.37 (dd, J=9.0 Hz, J=2.1 Hz), 6.44 (d, J=5.7 Hz, 1H), 6.15 (t, J=5.4 Hz, 1H), 3.88 (m, 1H), 3.69 (m, 1H + 2H), 3.58-3.37 (m, 4H), 2.74 (t, J=5.7 Hz, 2H), 2.40 (m, 1H), 1.90 (m, 3H), 1.51 (s, 3H), 1.13 (s, 3H) |
| 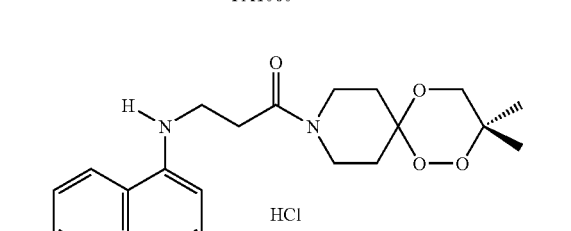 PA1061 | 68 (decomp.) | 300 MHz, 298 K, DMSOd$_8$: 14.26 (s, 1H), 9.49 (s, 1H), 8.65 (d, J=9.0 Hz), 8.54 (d, J=7.2 Hz), 8.06 (d, J=1.8 Hz, 1H), 7.77 (dd, J=9.3 Hz, J=1.8 Hz, 1H), 6.91 (d, J=7.2 Hz), 3.77-3.71 (m, 1H + 2H), 3.56-3.27 (m, 1H + 4H), 2.85 (t, J=6.6 Hz, 2H), 2.27-1.59 (m, 4H), 1.37 (s, 3H), 1.08 (s, 3H) |

TABLE-continued

| Compound | Melting point (° C.) | ¹H NMR (δ, ppm) |
|---|---|---|
| 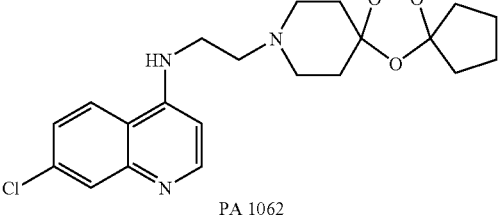 PA 1062 | 148 (decomp.) | 300 MHz, 298 K, CDCl$_3$: 8.52 (d, J=5.4 Hz, 1H), 8.00 (d, J=2.1 Hz, 1H), 7.68 (d, J=9.0 1H), 6.11 (broad s, 1H), 3.35 (broad s, 2H), 2.83 (m, 2H), 2.72 and 2.67 (2m, 2H and 2H), 1.93 (broad s, 2H + 2H + 2H + 2H), 1.67 (m, 2H + 2H) |
| 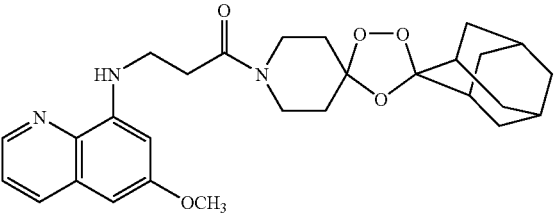 PA 1070 | 69 (decomp.) | 300 MHz, 298 K, CDCl$_3$: 8.56 (dd, J=4.2 Hz, J=1.8 Hz, 1H), 8.00 (dd, J=8.4 Hz, J=1.8 Hz, 1H), 7.35 (dd, J=8.4 Hz, J=4.2 Hz, 1H), 6.54 (broad s, 1H), 6.40 (2s, 1H + 1H), 3.91 (s, 3H), 3.87-3.47 (m, 2H + 2H + 2H), 2.80 (t, J=6.6 Hz, 2H), 2.00-1.70 (m, 2H + 2H + 14H) |
| 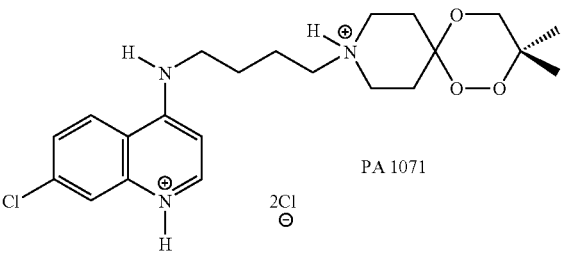 PA 1071 | 125 (decomp.) | 300 MHz, 298 K, DMSOd$_6$: 14.30 (s, 1H), 11.20 (s, 1H), 9.79 (s, 1H), 8.81 (d, J=9.0 Hz), 8.54 (d, J=6.9 Hz), 8.11 (s, 1H), 7.74 (dd, J=8.7 Hz, J=1.5 Hz, 1H), 6.88 (d, J=7.5 Hz), 3.75 (m, 1H), 3.65-3.40 (m, 2H + 1H + 2H), 3.14 (m, 2H), 2.92 (m, 2H), 2.25-1.79 (m, 4H + 2H), 1.75 (m, 2H), 1.38-1.06 (m, 6H) |
| 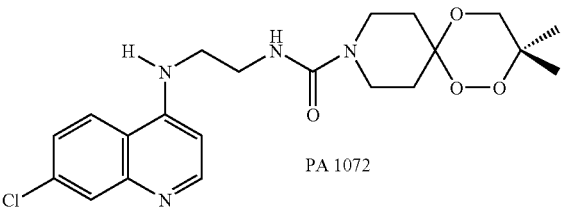 PA 1072 | 192 (decomp.) | 300 MHz, 298 K, CDCl$_3$: 8.48 (d, J=5.4 Hz, 1H), 7.92 (s, 1H), 7.86 (d, J=9.0 Hz, 1H), 7.37 (dd, J=8.7 Hz, J=1.8 Hz), 7.32 (s, 1H), 6.25 (d, J=5.4 Hz, 1H), 5.12 (t, J=5.7 Hz, 1H), 3.74 (m, 1H + 2H + 2H), 3.62-3.34 (m, 1H + 2H + 4H), 2.50-1.70 (m, 4H), 1.48 (s, 3H), 1.14 (s, 3H) |
| 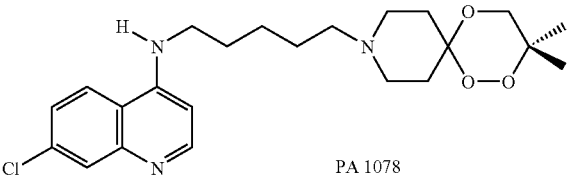 PA 1078 | 134 | 300 MHz, 298 K, CDCl$_3$: 8.55 (d, J=5.4 Hz, 1H), 7.97 (d, J=2.1 Hz, 1H), 7.66 (d, J=9.0 Hz, 1H), 7.38 (dd, J=8.7 Hz, J=2.1 Hz), 6.42 (d, J=5.4 Hz, 1H), 4.96 (s, 1H), 3.74 (broad s, 1H), 3.45 (broad s, 1H), 3.33 (q, J=7.2 Hz), 2.56 (m, 2H), 2.41 (m, 4H), 1.85-1.26 (m, 2H + 2H + 2H + 4H + 3H), 1.13 (s, 3H) |
| 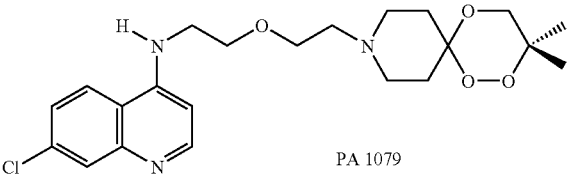 PA 1079 | 95 (decomp.) | 300 MHz, 298 K, CDCl$_3$: 8.55 (d, J=5.4 Hz, 1H), 7.97 (d, J=1.5 Hz, 1H), 7.72 (d, J=9.0 Hz, 1H), 7.40 (dd, J=9.0 Hz, J=1.2 Hz), 6.42 (d, J=5.1 Hz, 1H), 5.50 (s, 1H), 3.80 (m, 1H + 2H), 3.67 (t, J=5.4 Hz), 3.49 (m, 1H + 2H), 2.67 (m, 2H + 2H), 2.48 (m, 2H), 1.85 (m, 4H), 1.49 (s, 3H), 1.12 (s, 3H) |
| 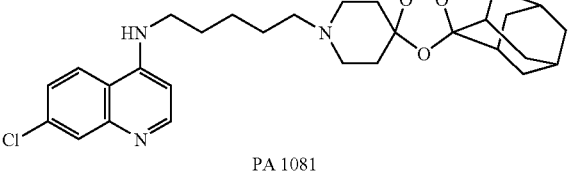 PA 1081 | 146 (decomp.) | 250 MHz, 298 K, CDCl$_3$: 8.52 (d, J=5.4 Hz, 1H), 7.96 (d, J=2.1 Hz, 1H), 7.69 (d, J=9.0 Hz, 1H), 7.37 (dd, J=9.0 Hz, J=2.1 Hz, 1H), 6.40 (d, J=5.4 Hz, 1H), 5.10 (broad s, 1H), 3.32 (m, 2H), 2.61-2.42 (m, 2H + 2H + 2H), 2.02-1.49 (m, 2H + 2H + 2H + 2H + 2H + 14H) |

| Compound | Melting point (° C.) | $^1$H NMR (δ, ppm) |
|---|---|---|
| 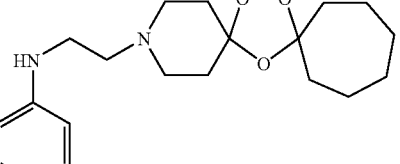 PA 1083 | 147 (decomp.) | 250 MHz, 298 K, CDCl$_3$: 8.52 (d, J=5.4 Hz, 1H), 7.99 (d, J=2.1 Hz, 1H), 7.64 (d, J=8.9 Hz, 1H), 7.39 (dd, J=8.9 Hz, J=2.1 Hz, 1H), 6.38 (d, J=5.4 Hz, 1H), 6.06 (broad s, 1H), 3.32 (m, 2H), 2.80 (m, 2H), 2.68 and 2.54 (2m, 2H and 2H), 1.91 (m, 2H + 2H + 2H + 2H), 1.67 (broad s, 2H + 2H + 2H + 2H) |
| 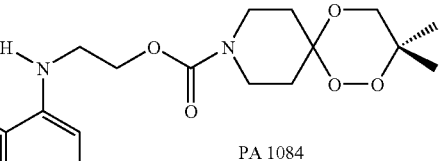 PA 1084 | 166 (decomp.) | 300 MHz, 298 K, CDCl$_3$: 8.55 (d, J=5.1 Hz, 1H), 7.96 (d, J=2.1 Hz, 1H), 7.73 (d, J=9.0 Hz, 1H), 7.39 (dd, J=9.0 Hz, J=2.1 Hz, 1H), 6.37 (d, J=5.4 Hz, 1H), 6.33 (s, 1H), 4.56 (m, 2H), 3.79-3.62 (m, 1H + 2H), 3.54 (q, J=4.5 Hz), 3.50-3.46 (m, 1H + 2H), 2.35 (m, 1H), 1.83-1.65 (m, 3H), 1.51 (s, 3H), 1.13 (s, 3H) |
| 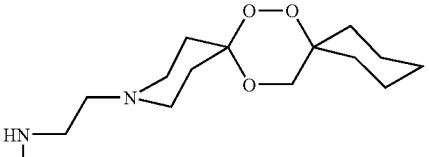 PA1110 | 151 (decomp.) | 300 MHz, 298 K, CDCl$_3$: 8.54 (d, J=5.4 Hz, 1H), 7.93 (d, J=2.1 Hz, 1H), 7.68 (d, J=9.0 Hz, 1H), 7.40 (dd, J=2.1 Hz, J=8.7 Hz, 1H), 6.39 (d, J=5.6 Hz, 1H), 5.97 (s, 1H), 3.78-3.48 (m, 2H), 3.33 (q, J=5.4 Hz, 2H), 2.81 (t, J=6.3 Hz), 2.70-2.48 (m, 4H), 2.20-1.20 (m, 4H + 10H + 3H + 3H) |
| 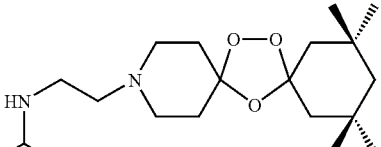 PA 1112 | 179 (decomp.) | 300 MHz, 298 K, CDCl$_3$: 8.55 (d, J=5.4 Hz, 1H), 8.00 (d, J=2.4 Hz, 1H), 7.67 (d, J=9.0 Hz, 1H), 7.41 (dd, J=9.0 Hz, J=2.4 Hz, 1H), 6.39 (d, J=5.4 Hz, 1H), 5.99 (broad s, 1H), 3.33 (m, 2H), 2.82 (m, 2H), 2.64 (m, 2H + 2H), 1.94 (t, J=5.7 Hz, 4H), 1.68 and 1.56 (2d, J=13.5 Hz, 2H and 2H), 1.32 (d, J=13.5 Hz, 1H), 1.22 (d, J=13.5 Hz, 1H), 1.06 (s, 6H), 1.04 (s, 6H) |
| 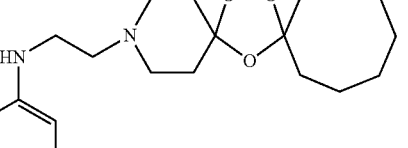 PA 1116 | 155 (decomp.) | 300 MHz, 298 K, CDCl$_3$: 8.55 (d, J=5.1 Hz, 1H), 7.99 (d, J=2.1 Hz, 1H), 7.65 (d, J=9.0 Hz, 1H), 7.40 (dd, J=9.0 Hz, J=2.1 Hz, 1H), 6.39 (d, J=5.1 Hz, 1H), 5.98 (broads, 1H), 3.32 (m, 2H), 2.82 (m, 2H), 2.82 (m, 2H), 2.72 and 2.58 (2m, 2H and 2H), 1.98 (m, 2H + 2H + 2H + 2H), 1.60 (m, 2H + 2H + 2H + 2H + 2H) |
| 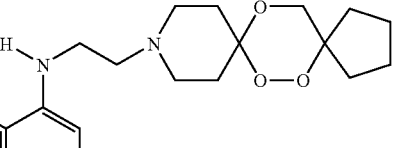 PA1120 | 145 | 300 MHz, 298 K, CDCl$_3$: 8.55 (d, J=5.4 Hz, 1H), 7.98 (d, J=2.1 Hz), 7.67 (d, J=9.0 Hz, 1H), 7.40 (dd, J=9.0 Hz, J=2.4 Hz), 6.39 (d, J=5.4 Hz, 1H), 5.99 (s, 1H), 4.02 (broad s, 1H), 3.53 (broad s, 1H), 3.33 (q, J=5.4 Hz, 2H), 2.81 (t, J=6.3 Hz, 2H), 2.70-2.40 (m, 4H), 2.13 (m, 4H + 8H) |

| Compound | Melting point (° C.) | $^1$H NMR (δ, ppm) |
|---|---|---|
| 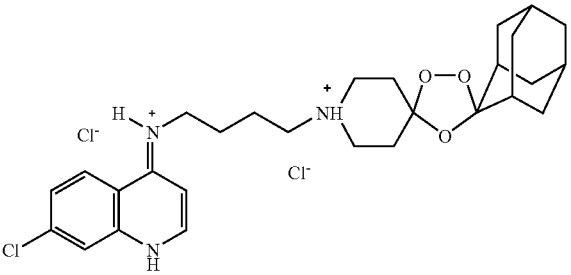 PA 1125 | 114 (decomp.) | 300 MHz, 298 K, DMSOd$_6$: 14.33 (broad s, 1H), 11.17 (broad s, 1H), 9.72 (broad s, 1H), 8.77 (d, J=9.0 Hz, 1H), 8.56 (d, J=7.2 Hz, 1H), 8.07 (d, J=1.8 Hz, 1H), 7.77 (dd, J=9.0 Hz, J=1.8 Hz, 1H), 6.91 (d, J=7.2 Hz, 1H), 3.56 (broad s, 2H), 3.45 and 3.00 (2m, 2H and 2H), 3.16 (broad s, 2H), 2.36-1.66 (m, 2H + 2H + 2H + 2H + 14H) |
| 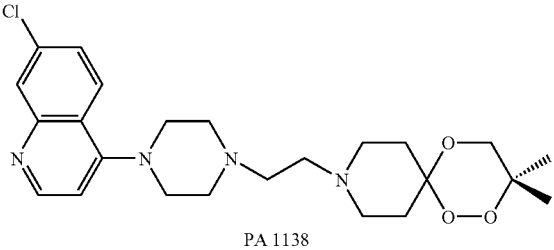 PA 1138 | n.d. | 300 MHz, 298 K, CDCl$_3$: 8.72 (d, J=5.1 Hz, 1H), 8.05 (d, J=2.1 Hz, 1H), 7.95 (d, J=9.0 Hz, 1H), 7.43 (dd, J=9.0 Hz, J=2.1 Hz, 1H), 6.84 (d, J=5.1 Hz, 1H), 3.81 (broad s, 1H), 3.46 (broad s, 1H), 3.27 (m, 2H), 2.88-2.80 (m, 4H), 2.72-2.63 (m, 6H), 2.53-2.40 (m, 4H), 2.19-1.80 (m, 4H), 1.52 (broad s, 3H), 1.13 (broad s, 3H) |
| 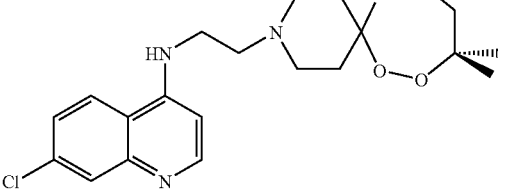 PA 1139 | 141 | 300 MHz, 298 K, CDCl$_3$: 8.52 (d, J=5.7 Hz, 1H), 8.03 (d, J=2.1 Hz, 1H), 7.72 (d, J=8.7 Hz, 1H), 7.41 (dd, J=9.0 Hz, J=2.1 Hz, 1H), 6.39 (d, J=5.7 Hz, 1H), 6.32 (broad s, 1H), 4.01-3.93 (m, 1H), 3.78-3.71 (m, 1H), 3.36 (t, J=5.7 Hz, 2H), 2.84 (t, J=6.3 Hz, 2H), 2.67-2.51 (m, 4H), 2.17 (m, 1H), 2.03-1.87 (m, 2H), 1.79-1.70 (m, 3H), 1.42 (s, 3H), 1.17 (s, 3H) |
| 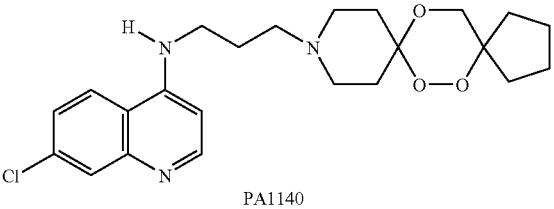 PA1140 | 151 | 300 MHz, 298 K, CDCl$_3$: 8.50 (d, J=5.4 Hz, 1H), 7.98 (d, J=2.1 Hz, 1H), 7.78 (d, J=9.0 Hz, 1H), 7.73 (broad s, 1H), 7.38 (dd, J=9.0 Hz, J=2.1 Hz, 1H), 6.34 (d, J=5.4 Hz, 1H), 4.00 (m, 1H), 3.55 (m, 1H), 3.41 (q, J=5.7 Hz, 2H), 2.77-2.40 (m, 6H + 2H), 2.20-1.44 (m, 8H + 2H + 2H) |
| 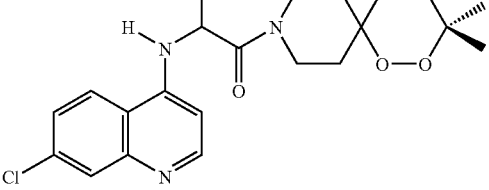 PA1141 | 176 | 300 MHz, 298 K, CDCl$_3$: 8.52 (d, J=5.4 Hz, 1H), 7.97 (d, J=2.1 Hz, 1H), 7.82 (d, J=9.0 Hz, 1H), 7.40 (dd, J=8.7 Hz, J=2.1 Hz, 1H), 6.56 (d, J=6.6 Hz, 1H), 6.34 (d, J=5.4 Hz, 1H), 4.59 (qd, J=6.6 Hz, 1H), 4.04-3.47 (m, 2H + 4H), 2.50 (m, 1H), 2.18-1.86 (m, 3H), 1.56 (broad s, 3H), 1.51 (d, J=6.3 Hz, 3H), 1.23 (broad s, 3H) |
| 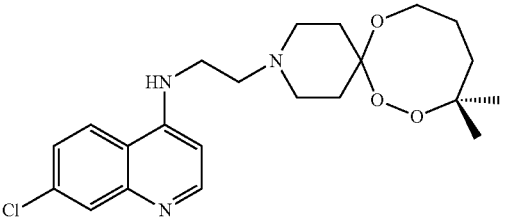 PA1142 | 112 | 300 MHz, 298 K, CDCl$_3$: 8.52 (d, J=5.4 Hz, 1H), 8.03 (m, 1H), 7.73 (dd, J=3.0 Hz, J=9.0 Hz, 1H), 7.42 (dd, J=9.0 Hz, J=2.1 Hz, 1H), 6.40 (d, J=5.7 Hz, 1H), 6.40 (broad s, 1H), 3.95-3.90 (m, 1H), 3.72-3.62 (m, 1H), 3.37 (s, 2H), 2.86 (t, J=5.1 Hz, 2H), 2.69-2.60 (m, 4H), 2.15-2.00 (m, 3H), 1.82 (t, J=5.7 Hz, 2H), 1.73 (t, J=4.2 Hz, 2H), 1.64-1.58 (m, 1H), 1.34 (s, 3H), 1.14 (s, 3H) |

TABLE-continued

| Compound | Melting point (° C.) | $^1$H NMR (δ, ppm) |
|---|---|---|
| PA1143 | 149 (decomp) | 300 MHz, 298 K, CDCl$_3$: 8.52 (d, J=5.4 Hz, 1H), 8.04 (s, 1H), 7.77 (d, J=9.0 Hz, 1H), 7.42 (dd, J=9.0 Hz, J=2.4 Hz, 1H), 6.47 (d, J=5.7 Hz, 1H), 6.24 (broad s, 1H), 3.81-3.68 (m, 1H + 1H), 3.50 (m, 1H), 2.74-2.38 (m, 6H + 2H), 2.00-1.70 (m, 2H), 1.50 (broad s, 3H), 1.35 (d, J=6.0 Hz, 3H), 1.12 (broad s, 3H) |

The study of the pharmacological properties of the coupling products of formula (I) according to the invention has shown that they exhibit antimalarial activity.

The obtaining of such an effect is all the more advantageous since phenomena of resistance to strains of *Plasmodium falciparum*, the deadly species, with respect to the usual antimalarial medicinal products are developing, and since, in addition, protection through vaccines, for which considerable research is being carried out, may not be realized for several years.

Study of the Antimalarial Activity of the Dual Molecules According to the Invention on *P. falciparum*

The results obtained in vitro on *P. falciparum* cultured in human red blood cells are given below.

1. *P. falciparum* Culture

The *P. falciparum* strains are cultured continuously according to the method of Trager and Jensen (Science, 1976, 193, 673-675): the parasites are maintained in human red blood cells (O±), diluted to a blood parasite level of 2% in RPMI 1640 medium supplemented with 25 mM of Hepes+24 mM NaHCO$_3$+2 mM L-glutamine and with 5% of human serum of all groups. The parasites are incubated at 37° C. in a humid atmosphere and at 5% CO$_2$. The FcB1-Columbia and FcM29-Cameroon strains are, respectively, moderately (IC$_{50}$: 66 nM) and very strongly (IC$_{50}$: 258 nM) chloroquine resistant. The IC$_{50}$ values for artemisinin on these 2 strains are, respectively, 11 nM and 5 nM.

2. Chemosensitivity Test

The antimalarial activity tests are carried out according to the radioactive micromethod of Desjardins et al. (*Antimicrob. Agents Chemother.*, 1979, 16, 710-718). Each molecule is tested in triplicate. The assays are carried out in 96-well microplates. The *P. falciparum* strains are cultured in solutions of RPMI 1640 supplemented with 5% of human serum with a haematocrit at 2% and a blood parasite level at 1.5%. For each assay, the parasites are incubated with decreasing concentrations of the test compounds for 48 h at 37° C., in a humid atmosphere and at 5% CO$_2$. Artemisinin and chloroquine diphosphate are used as reference molecules. The first dilution of the test compounds is effected at 1 mg/ml in dimethyl sulphoxide. The dilution range for the successive daughter solutions is also prepared in dimethyl sulphoxide. Each daughter dilution is then diluted to $\frac{1}{50}^{th}$ in RPMI 1640 supplemented with 5% of human serum, all the dilutions being carried out at 37° C. These dilutions are then added to the parasites in culture in the microplates. After addition of the test compound, the parasites are cultured in RPMI 1640 containing 5% of human serum and 1% of dimethyl sulphoxide. The parasite growth is measured by incorporation of tritiated hypoxanthine (added 24 h after the beginning of exposure to the test compound) and compared to the incorporation in the absence of the test compound (taken as 100%). The IC$_{50}$ values (concentrations required to inhibit parasite growth by 50%) are determined by plotting the percentage inhibition as a function of the logarithm of the dose, using the GraphPad Prism 4® processing software (GraphPad Software Inc., 5755 Oberlin Drive, #110, San Diego, Calif. 92121, USA).

3. Results

The IC$_{50}$ values for the compounds of formula (I) according to the invention are less than 1 μM. On the strains used, these IC$_{50}$ values are, for most of the compounds of formula (I) tested, comparable to those of artemisinin, or even better.

No notable difference is measured between the IC$_{50}$ values for the compounds tested on one or other of the strains, i.e. on the FcB1-Colombia strain (strain moderately resistant to chloroquine) and on the FcM29-Cameroon strain (strain highly resistant to chloroquine).

By way of examples, the IC$_{50}$ values for the compounds PA1011, PA1021 and PA1026 on the FcM29-Cameroon strain are, respectively, equal to 13 nM, 6 nM and 4.4 nM.

The invention is directed towards exploiting the properties of these coupling products for their use as medicinal products and for the development of pharmaceutical compositions with antimalarial properties.

Thus, according to another of its aspects, a subject of the invention is medicinal products which comprise a compound of formula (I), or an addition salt of the latter with a pharmaceutically acceptable acid, or else a hydrate or a solvate of the compound of formula (I).

These medicinal products are of use in therapeutics, in the prevention and treatment of malaria.

According to another of its aspects, the present invention relates to pharmaceutical compositions comprising, as active principle, a compound according to the invention. These pharmaceutical compositions contain an effective dose of at least one compound of formula (I) according to the invention, or a pharmaceutically acceptable salt, a hydrate or a solvate of said compound, and also at least one pharmaceutically acceptable excipient. Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its possible salt, solvate or hydrate, can be administered in a unit administration form, as a mixture with conventional pharmaceutical excipients, for the prevention or treatment of malaria.

The suitable unit administration forms comprise the oral administration forms such as tablets, soft or hard gelatin capsules, powders, granules and oral solutions or suspensions, the sublingual, buccal, intratracheal, intraocular or intranasal administration forms and the form for administration by inhalation, the topical, transdermal, subcutaneous, intramuscular or intravenous administration forms, the rectal administration forms, and implants. For topical application, the compounds according to the invention can be used in creams, gels, ointments or lotions. Preferred routes of administration are oral, rectal and injectable routes.

By way of example, a unit administration form of a compound according to the invention in tablet form can comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

There may be specific cases where higher or lower doses are appropriate; such doses do not depart from the context of the invention. According to usual practice, the dose suitable for each patient is determined by the physician according to the mode of administration and the weight and response of said patient.

According to another of its aspects, the present invention also relates to a method for treating or preventing malaria, which comprises the administration, to a patient, of an effective dose of a compound of formula (I) according to the invention, or one of its pharmaceutically acceptable salts or hydrates or solvates.

The invention is also directed towards the biological reagents for which the active principles consist of the compounds according to the invention. These reagents can be used as references or standards in any antimalarial activity studies.

What is claimed is:

1. A compound corresponding to formula (I):

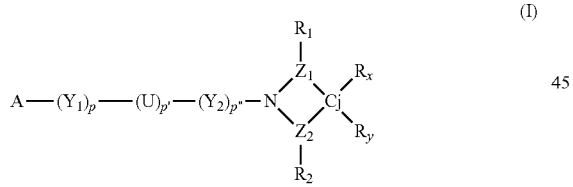

(I)

in which:
A represents a residue of a molecule with antimalarial activity and/or a residue that facilitates the bioavailability wherein A represents an aminoquinoline of formula (IIb):

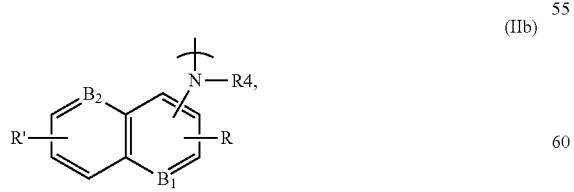

(IIb)

in which,
$B_1$ is N and $B_2$ is =CH—;
R and R', which may be identical or different, each represent one or more substituents occupying distinct positions on the rings to which they are attached, chosen from hydrogen or halogen atoms and the groups —OH, —$CF_3$, aryl, heteroaryl, alkyl or —O-alkyl, —$NO_2$ or —N(Ra,Rb), where Ra and Rb, which may be identical or different, represent hydrogen atoms or alkyl groups containing from 1 to 5 carbon atoms and being linear or branched; at least one of R or R' being different from a hydrogen atom;
R4 represents a hydrogen atom or a linear or branched C1 to C5 alkyl radical,
in the form of a base or of an addition salt with an acid;
p represents 1, p' and p" represents 0 or 1,
$Y_1$ and $Y_2$, which may be identical or different, represent a linear $C_1$ to $C_6$ alkylene chain optionally comprising one or more carbonyl, thiocarbonyl ether or thioether radicals,
U represents an amine, amide, thioamide, sulphonyl, sulphonate, sulphonamide, carbonyl, thiocarbonyl, carboxyl, thiocarboxyl, ether or thioether radical,
$Z_1$ and $Z_2$, which may be identical or different, represent a saturated linear $C_1$ to $C_4$ alkylene radical, and Cj represens carbon,
$R_1$ and $R_2$, which may be identical or different, represent a hydrogen atom or a functional group capable of increasing the water-solubility of the dual molecule,
$R_x$ and $R_y$, together form a cyclic peroxide wherein, $R_x$ and $R_y$, together form a cyclic peroxide corresponding to formula (XI),

(XI)

said cyclic peroxide being substituted with 1 to 4 groups $R_3$, which may be identical or different from one another, occupying any positions on the carbon atoms of the peroxide ring and being chosen from the following atoms and groups:
hydrogen, halogen, —OH, —$CF_3$, —$NO_2$, aryl or heteroaryl, ($C_3$-$C_8$) cycloalkyl, alkyl or —O-alkyl, said alkyl groups containing from 1 to 10 carbon atoms and being linear or branched,
at least one of the groups $R_3$ being different from a hydrogen atom,
in the form of a base or of an addition salt with an acid.

2. A compound of formula (I) according to claim 1, wherein, A represents an aminoquinoline of formula (IIa):

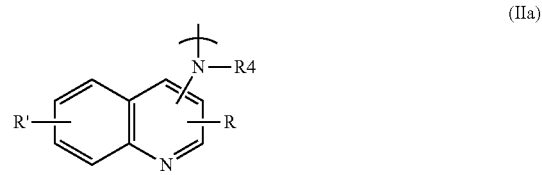

(IIa)

in which
R and R', which may be identical or different, each represent one or more substituents occupying distinct positions on the rings to which they are attached, chosen from hydrogen or halogen atoms and the groups —$CF_3$, or —N($R_a$,$R_b$), where $R_a$ and $R_b$, which may be identical or different, represent hydrogen atoms or alkyl groups containing from 1 to 5 carbon atoms and being linear or branched; at least one of R or R' being different from a hydrogen atom;

$R_4$ represents a hydrogen atom or a linear or branched $C_1$ to $C_5$ alkyl radical in the form of a base or of an addition salt with an acid.

3. A compound of formula (I) according to claim 1, wherein $R_x$ and $R_y$ together form a cyclic peroxide corresponding to formula (XIc):

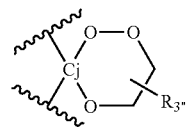

(XIc)

in which $R_{3''}$ represents 1 to 4 groups, which may be identical or different from one another, occupying any positions on the carbon atoms of the peroxide ring and being chosen from the following atoms and groups:

hydrogen or alkyl said alkyl groups containing from 1 to 10 carbon atoms,-at least one of the groups $R_{3''}$ being different from a hydrogen atom, in the form of a base or of an addition salt with an acid.

4. A compound of formula (I) according to claim 1, wherein it corresponds to formula (XIII):

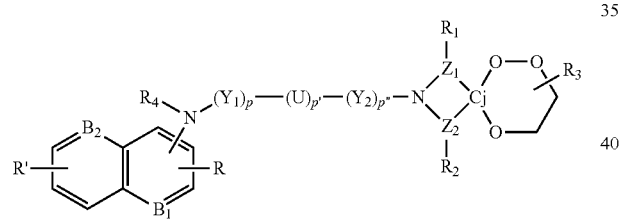

(XIII)

in which R, R', $B_1$, $B_2$, $Y_1$, U, $Y_2$, p, p', p'', $Z_1$, $Z_2$, $R_1$, $R_2$, $R_3$ and $R_4$ are as defined in claim 1, in the form of a base or of an addition salt with an acid.

5. A compound of formula (I) according to claim 1, wherein:

—$Y_1$ is $C_1$ to $C_6$ alkylene chain optionally comprising carbonyl or ether radicals, in the form of a base or of an addition salt with an acid.

6. A compound of formula (I) according to claim 5, wherein:

p'=p''-=0, p=1 and $Y_1$ represents a linear $C_1$ to $C_6$ alkylene chain in the form of a base or of an addition salt with an acid.

7. A compound of formula (I) according to claim 1, wherein $Z_1$ and $Z_2$, which may be identical or different, each represent a linear $C_1$ to $C_4$ alkylene radical, in the form of a base or of an addition salt with an acid.

8. A compound of formula (I) according to claim 1, wherein it corresponds to formula (XV):

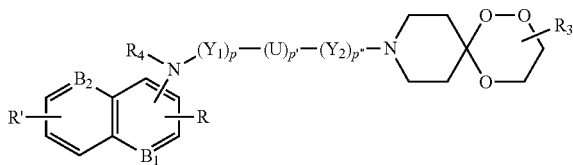

(XV)

in which R, R', $B_1$, $B_2$, $Y_1$, U, $Y_2$, p, p', p'', $R_1$, $R_2$, $R_3$ and $R_4$ are as defined in claim 1, in the form of a base or of an addition salt with an acid.

9. A compound of formula (I) according to claim 1, wherein it is chosen from

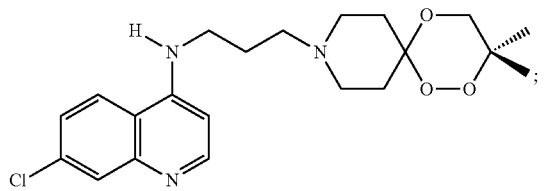

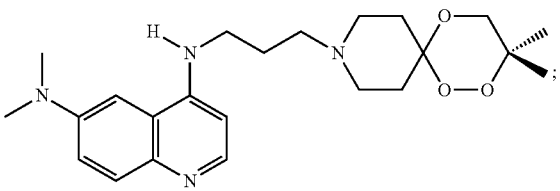

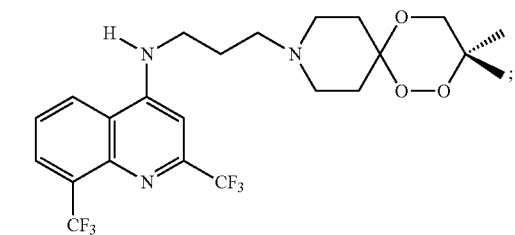

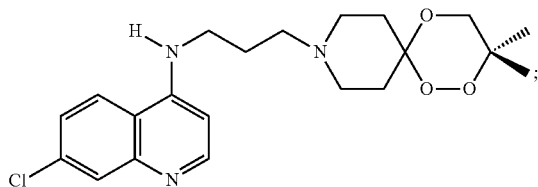

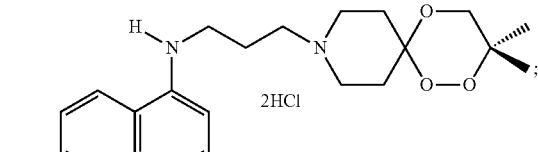

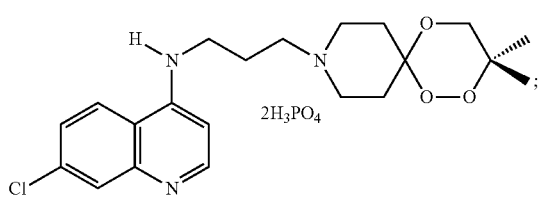

-continued

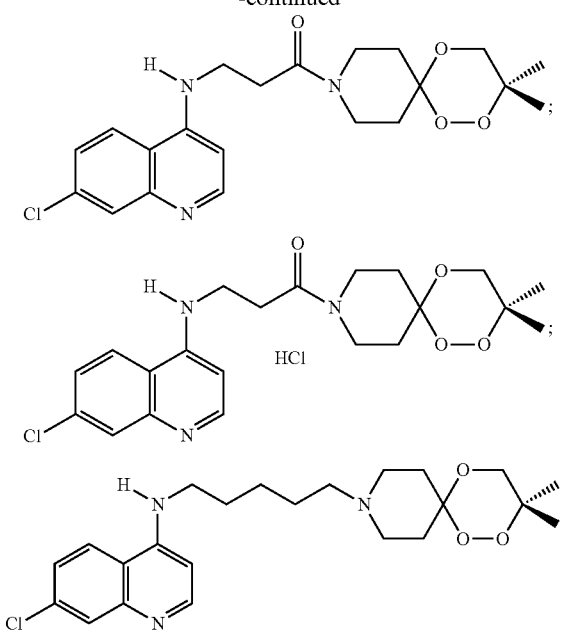

and

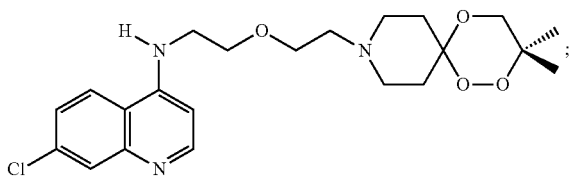

in the form of a base or of an addition salt with an acid.

10. A process for preparing a compound of formula (I) according to claim 1, wherein it comprises the reaction of reactive derivatives of A and of peroxide derivatives comprising the residues $R_x$ and $R_y$, so as to form, between these derivatives, a coupling arm $(Y_1)_p$—$(U)_{p'}$—$(Y_2)_{p''}$ as defined in claim 1.

11. A preparation process according to claim 10, wherein, to prepare compounds containing, as derivative A, an aminoquinoline of formula (IIa)

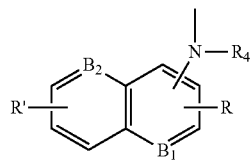

(IIa)

in which

R and R', which may be identical or different, each represent one or more substituents occupying distinct positions on the rings to which they are attached, chosen from hydrogen or halogen atoms and the groups —OH, —CF$_3$, aryl, heteroaryl, alkyl or —O-alkyl, —NO$_2$ or —N($R_a$,$R_b$), where $R_a$ and $R_b$, which may be identical or different, represent hydrogen atoms or alkyl groups containing from 1 to 5 carbon atoms and being linear, branched or cyclic; at least one of R or R' being different from a hydrogen atom;

$R_4$ represents a hydrogen atom or a linear or branched C$_1$ to C$_5$ alkyl radical, a compound of formula (XVII):

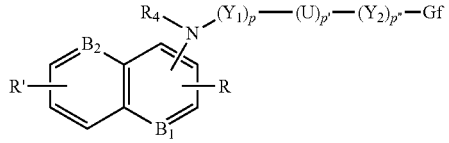

(XVII)

in which, $Y_1$, $Y_2$, U, p, p' and p'' are is as defined in claim 1 and Gf represents a functional group,
is reacted with a compound of formula (XVIII)

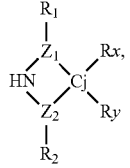

(XVIII)

in which $Z_1$, $Z_2$, $R_1$, $R_2$, Cj, $R_x$ and $R_y$ are as defined in claim 1.

12. A preparation process according to claim 10, wherein, to prepare compounds in which p=1 and which contain, as derivative A, an aminoquinoline of formula (IIa)

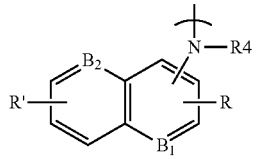

(IIa)

in which

R and R', which may be identical or different, each represent one or more substituents occupying distinct positions on the rings to which they are attached, chosen from hydrogen or halogen atoms and the groups —OH, —CF$_3$, aryl, heteroaryl, alkyl or —O-alkyl, —NO$_2$ or —N($R_a$,$R_b$), where $R_a$ and $R_b$, which may be identical or different, represent hydrogen atoms or alkyl groups containing from 1 to 5 carbon atoms and being linear, branched or cyclic; at least one of R or R' being different from a hydrogen atom;

$R_4$ represents a hydrogen atom or a linearbranched C$_1$ to C$_5$ alkyl radical, $B_1$ represents a nitrogen atom and $B_2$ represents a —CH= ring member, a compound of formula (XIX):

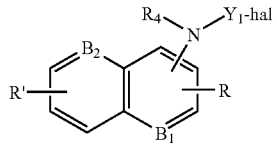

(XIX)

in which $Y_1$ is as defined in claim 1, and "hal" represents a halogen atom,
is reacted with a compound of formula (XX),

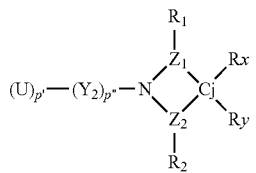

(XX)

in which U, $Y_2$, p', p'', $Z_1$, $Z_2$, $R_1$, $R_2$, Cj, $R_x$ and $R_y$ are as defined in claim 1.

13. A pharmaceutical composition, wherein, it comprises a compound of formula (I) according to claim 1, or a pharmaceutically acceptable salt, and also at least one pharmaceutically acceptable excipient.

14. A method for the treatment or prevention of malaria comprising administering to a patient in need of such treatment, a pharmaceutically effective amount of a compound according to claim 1.

15. A method for the treatment of malaria comprising administering to a patient in need of such treatment, a pharmaceutically effective amount of a pharmaceutical composition according to claim 13.

* * * * *

UNITED STATES PATENT AND TRADEMARK OFFICE
CERTIFICATE OF CORRECTION

PATENT NO. : 7,947,701 B2
APPLICATION NO. : 11/433890
DATED : May 24, 2011
INVENTOR(S) : Jerome Cazelles et al.

It is certified that error appears in the above-identified patent and that said Letters Patent is hereby corrected as shown below:

In column 5, line 26, delete "$R_1$" and insert -- $R'$ --, therefor.

In column 5, line 32, delete "$R_1$" and insert -- $R'$ --, therefor.

In column 8, line 60, delete "$R_{3'}$" and insert -- $R_{3''}$ --, therefor.

In column 9, line 11, delete "$R_{3'}$" and insert -- $R_{3''}$ --, therefor.

In column 9, line 13, delete "$R_{3'}$" and insert -- $R_{3''}$ --, therefor.

In column 10, line 34, delete "$R_3$," and insert -- $R_{3'}$ --, therefor.

In column 11, line 43, delete "$R_3$," and insert -- $R_{3'}$ --, therefor.

In column 14, line 14, delete "p"0" and insert -- p"=0 --, therefor.

In column 17, line 38, delete "$ACC_{6-35}$" and insert -- ACC 6-35 --, therefor.

In column 18, line 60, delete "$ACC_{6-35}$" and insert -- ACC 6-35 --, therefor.

In column 20, line 1, delete "HC13), HC14)," and insert -- HC13, HC14), --, therefor.

In column 20, line 9, delete "100))." and insert -- 100). --, therefor.

In column 21, line 19, delete "100))." and insert -- 100). --, therefor.

In column 23, line 58, delete "$CDCl_3$) 8, ppm:" and insert -- $CDCl_3$) δ, ppm: --, therefor.

In column 23, line 64, delete "(MH+100)." and insert -- ($MH^+$, 100). --, therefor.

Signed and Sealed this
Tenth Day of January, 2012

David J. Kappos
*Director of the United States Patent and Trademark Office*

CERTIFICATE OF CORRECTION (continued)

In column 24, line 66, delete "M/Z" and insert -- m/z --, therefor.

In column 35, line 46, delete "CDCl₃) 6, ppm:" and insert -- CDCl$_3$) δ, ppm: --, therefor.

In column 36, line 20, delete "-4,3,-" and insert -- -4,3'- --, therefor.

In column 43-44, line 35, delete "DMSOd₈:" and insert -- DMSOd$_6$: --, therefor.

In column 45-46, line 41, delete "DMSOd₈:" and insert -- DMSOd$_6$: --, therefor.

In column 55, line 19, delete "croscaramellose" and insert -- croscarmellose --, therefor.

In column 55, line 56-61, in Structure IIb, in claim 1, delete " 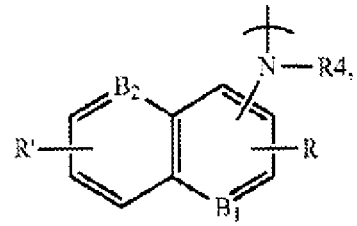 " and insert -- 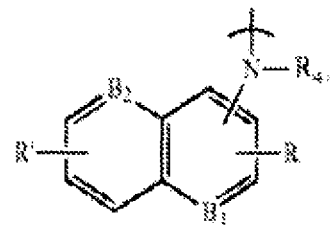 --, therefor.

In column 56, line 21, in claim 1, delete "represens" and insert -- represents --, therefor.

In column 56, line 54-59, in Structure, in claim 2, delete " 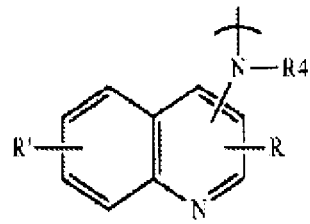 " and insert -- 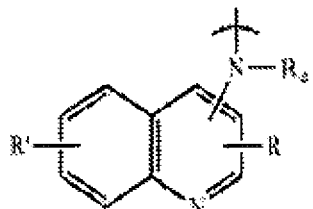 --, therefor.

In column 57, line 26, in claim 3, delete "-at" and insert -- at --, therefor.

CERTIFICATE OF CORRECTION (continued)
U.S. Pat. No. 7,947,701 B2

In column 57, line 45, in claim 4, after "$Z_2$," insert -- $C_j$, --.

In column 57, line 57, in claim 6, delete "p'=p"-=0," insert -- p'=p"=0, --.

In column 59, line 30, in claim 9, after " 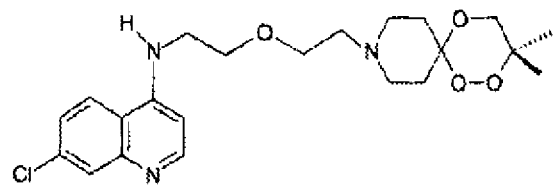 " delete ";".

In column 60, line 25-32, in claim 12, delete " 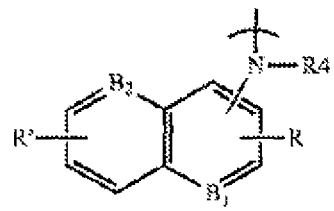 " and insert -- 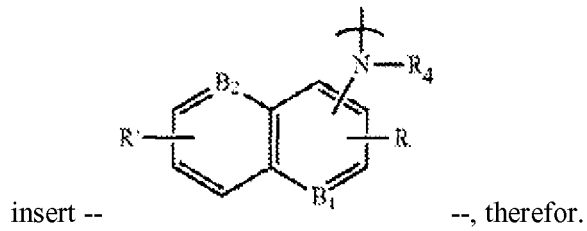 --, therefor.

In column 60, line 43, in claim 12, delete "linearbranched" and insert -- linear or branched --, therefor.

In column 61, line 6, in claim 14, after "treatment" delete "or prevention".